(12) United States Patent  (10) Patent No.: US 7,915,292 B2
Guillemont et al.  (45) Date of Patent: Mar. 29, 2011

(54) ANTIBACTERIAL QUINOLINE DERIVATIVES

(75) Inventors: Jérôme Emile Georges Guillemont, Ande (FR); David Francis Alain Lançois, Louviers (FR); Elisabeth Thérèse Jeanne Pasquier, Le Neubourg (FR); Koenraad Jozef Lodewijk Marcel Andries, Beerse (BE); Anil Koul, Berchem (BE)

(73) Assignee: Janssen Pharmaceutica NV, Beerse (BE)

( * ) Notice: Subject to any disclaimer, the term of this patent is extended or adjusted under 35 U.S.C. 154(b) by 467 days.

(21) Appl. No.: 11/996,786

(22) PCT Filed: Jul. 26, 2006

(86) PCT No.: PCT/EP2006/064656
§ 371 (c)(1),
(2), (4) Date: Jan. 25, 2008

(87) PCT Pub. No.: WO2007/014885
PCT Pub. Date: Feb. 8, 2007

(65) Prior Publication Data
US 2008/0182855 A1   Jul. 31, 2008

(30) Foreign Application Priority Data

Jul. 28, 2005  (EP) .................... 05106962

(51) Int. Cl.
C07D 215/00 (2006.01)
A61K 31/472 (2006.01)
(52) U.S. Cl. ........................ 514/314; 546/176
(58) Field of Classification Search ........... 546/176; 514/314
See application file for complete search history.

(56) References Cited

FOREIGN PATENT DOCUMENTS

JP     01063518 A * 3/1989
WO    WO 2004/011436 A1  2/2004

OTHER PUBLICATIONS

Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutices, 3ed." Marcel Dekker, New York, 1996, pp. 451 and 596.*
International Search Report dated Oct. 6, 2006 for related International Application No. PCT/EP2006/064656.

* cited by examiner

Primary Examiner — Kahsay T Habte

(57) ABSTRACT

The present invention relates to novel substituted quinoline derivatives according to the general Formula (Ia) or Formula (Ib):

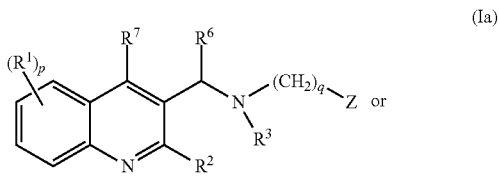

(Ia)

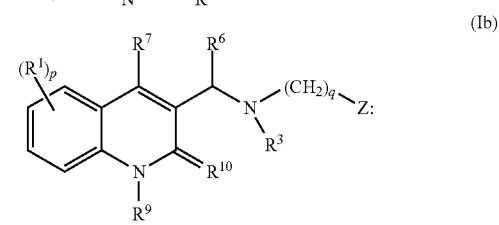

(Ib)

the pharmaceutically acceptable acid or base addition salts thereof, the quaternary amines thereof, the stereochemically isomeric forms thereof, the tautomeric forms thereof and the N-oxide forms thereof. The claimed compounds are useful for the treatment of a bacterial disease including a mycobacterial disease, particularly those diseases caused by pathogenic mycobacteria such as *Mycobacterium tuberculosis, M. bovis, M. avium* and *M. marinum*. Also claimed is a composition comprising a pharmaceutically acceptable carrier and, as active ingredient, a therapeutically effective amount of the claimed compounds, the use of the claimed compounds or compositions for the manufacture of a medicament for the treatment of bacterial diseases and a process for preparing the claimed compounds.

12 Claims, No Drawings

ANTIBACTERIAL QUINOLINE DERIVATIVES

CROSS REFERENCE TO RELATED APPLICATIONS

This application is a national stage application of Patent Application No. PCT/EP2006/064656, filed Jul. 26, 2006, which in turn claims the benefit of EPO Patent Application No. 05106962.3 filed Jul. 28, 2005. The complete disclosures of the aforementioned related patent applications are hereby incorporated herein by reference for all purposes.

The present invention relates to novel substituted quinoline derivatives useful for the treatment of bacterial diseases, including but not limited to diseases caused by pathogenic mycobacteria such as *Mycobacterium tuberculosis, M. bovis, M. avium* and *M. marinum*.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epithelioid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is patho-physiological environment in human lesions namely, reduced oxygen tension, nutrient limitation, and acidic pH. These factors have been postulated to render these bacteria phenotypically tolerant to major antimycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

WO 2004/011436, WO2005/070924, WO2005/070430 and WO2005/075428 disclose certain substituted quinoline derivatives having activity against *Mycobacteria*, in particular against *Mycobacterium tuberculosis*. One particular compound of these substituted quinoline derivatives is described in Science (2005), 307, 223-227.

Other substituted quinolines are disclosed in U.S. Pat. No. 5,965,572 (The United States of America) for treating antibiotic resistant infections and in WO 00/34265 to inhibit the growth of bacterial microorganisms.

The purpose of the present invention is to provide novel compounds, in particular substituted quinoline derivatives, having the property of inhibiting bacterial growth especially of mycobacteria and therefore useful for the treatment of mycobacterial diseases, particularly those diseases caused by pathogenic mycobacteria such as *Mycobacterium tuberculosis* (including the latent disease and including drug resistant *M. tuberculosis* strains), *M. bovis*, *M. avium* and *M. marinum*. The compounds are also useful in the treatment of other bacterial infections as described below.

The compounds according to the present invention are characterized by the presence of a tertiary nitrogen atom in the alpha position in the side chain attached to the 3-position of the quinoline nucleus and thus have a different basic structure to the quinoline derivatives described in the above-mentioned WO 2004/011436 which have an asymmetric carbon atom in this position. The compounds according to the present invention therefore have the advantage that they are able to form fewer enantiomers than the compounds in WO 2004/011436.

SUMMARY OF THE INVENTION

The present invention relates to novel substituted quinoline derivatives according to Formula (Ia) or Formula (Ib):

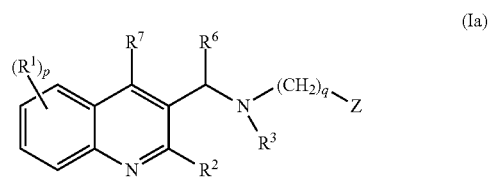

(Ia)

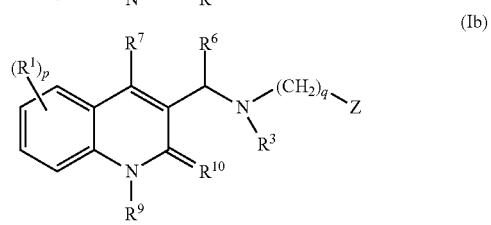

(Ib)

the pharmaceutically acceptable acid or base addition salts thereof, the quaternary amines thereof, the stereochemically isomeric forms thereof, the tautomeric forms thereof, the N-oxide forms thereof or pro-drugs thereof, wherein:
p is an integer equal to zero, 1, 2, 3 or 4;
q is an integer equal to 1, 2 or 3;
Z is a radical selected from formulae:

(a)

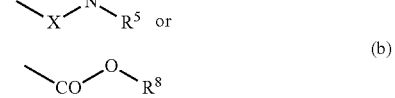

(b)

$R^1$ is cyano, halo, alkyl, haloalkyl, hydroxy, alkyloxy, alkylthio, alkyloxyalkyl, alkylthioalkyl, arylalkyl, di(aryl)alkyl, aryl or Het;
$R^2$ is hydrogen, alkyloxy, aryl, aryloxy, hydroxy, mercapto, alkyloxyalkyloxy, alkylthio, mono or di(alkyl)amino, pyrrolidino or a radical of formula

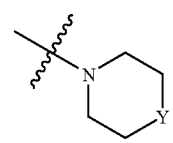

wherein Y is $CH_2$, O, S, NH or N-alkyl;
$R^3$ is alkyl, arylalkyl, aryl, mono- or di-alkylaminoalkyl, Het or Het-alkyl;
$R^4$ and $R^5$ each independently is hydrogen; alkyl; alkyloxyalkyl; arylalkyl; Het-alkyl; mono- or dialkylaminoalkyl; Het; or aryl; or $R^4$ and $R^5$ together with the nitrogen atom to which they are attached form a radical selected from the group consisting of pyrrolidino, piperidino, piperazino, morpholino, 4-thiomorpholino, 2,3-dihydroisoindol-1-yl, thiazolidin-3-yl, 1,2,3,6-tetrahydropyridyl, 1,4-diazacycloheptyl, 1-aza-4-oxacycloheptyl, 1,2,3,4-tetrahydroisoquinolin-2-yl, 2H-pyrrolyl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, optionally substituted with one or more substituents, each substituent independently selected from alkyl, haloalkyl, halo, arylalkyl, hydroxy, alkyloxy, amino, mono- or dialkylamino, alkylthio, alkyloxyalkyl, alkylthioalkyl, aryl, pyridyl or pyrimidinyl;

$R^6$ is aryl or Het;

$R^7$ is hydrogen, halo, alkyl, aryl or Het;

$R^8$ is a straight or branched saturated hydrocarbon radical having from 1 to 6 carbon atoms;

$R^9$ is hydrogen or alkyl;

$R^{10}$ is oxo; and

X is —$CH_2$— or —CO—;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with cyano, hydroxy, alkyloxy or oxo;

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, carboxyl, alkyloxycarbonyl, aminocarbonyl, morpholinyl or mono- or dialkylaminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, alkyl or alkyloxy;

halo is a substituent selected from fluoro, chloro, bromo or iodo; and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms.

Unless otherwise indicated, the above compounds according to Formula (Ia) or Formula (Ib), the pharmaceutically acceptable acid or base addition salts thereof, the quaternary amines thereof, the stereochemically isomeric forms thereof, the tautomeric forms thereof, the N-oxide forms thereof or pro-drugs thereof, are hereinafter referred to as the compounds according to the invention.

The compounds according to Formula (Ia) and (Ib) are interrelated in that e.g. a compound according to Formula (Ib), with $R^{10}$ equal to oxo is the tautomeric equivalent of a compound according to Formula (Ia) with $R^2$ equal to hydroxy (keto-enol tautomerism).

In the definition of Het, it is meant to include all the possible isomeric forms of the heterocycles, for instance, pyrrolyl comprises 1H-pyrrolyl and 2H-pyrrolyl.

The aryl or Het listed in the definitions of the substituents of the compounds of formula (Ia) or (Ib) (see for instance $R^3$) as mentioned hereinbefore or hereinafter may be attached to the remainder of the molecule of formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable acid addition salts are defined to comprise the therapeutically active non-toxic acid addition salt forms which the compounds according to Formula (Ia) or Formula (Ib) are able to form. Said acid addition salts can be obtained by treating the base form of the compounds according to Formula (Ia) or Formula (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (Ia) or Formula (Ib) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (Ia) or Formula (Ib) as well as the salts thereof, are able to form. Such solvates are, for example, hydrates and alcoholates.

The term "quaternary amine" as used hereinbefore defines the quaternary ammonium salts which the compounds of formula (Ia) or (b) are able to form by reaction between a basic nitrogen of a compound of formula (Ia) or (b) and an appropriate quaternizing agent, such as, for example, an optionally substituted alkylhalide, arylalkylhalide, alkylcarbonylhalide, Arcarbonylhalide, Hetalkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, alkyl and Ar. Preferably, the quaternizing agent is alkylhalide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

The term "stereochemically isomeric forms" as used hereinbefore or hereinafter defines all the possible stereoisomeric forms which the compounds of formula (Ia) and (Ib), and their N-oxides, addition salts or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (Ia) and (Ib) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (αS, βR), this means that the compound is substantially free of the (αR, βS) isomer.

The compounds of either formula (Ia) and (Ib) may be synthesized in the form of racemic mixtures of enantiomers which can be separated from one another following art-known resolution procedures. The racemic compounds of either formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of Formula (Ia) or Formula (Ib) are meant to comprise those compounds of Formula (Ia) or Formula (Ib) wherein e.g. an enol group is converted into a keto group (keto-enol tautomerism).

The N-oxide forms of the present compounds are meant to comprise the compounds of formula (Ia) or (Ib) wherein one or several tertiary nitrogen atoms are oxidized to the so-called N-oxide.

The compounds of formula (Ia) and (Ib) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (Ia) or Formula (Ib), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

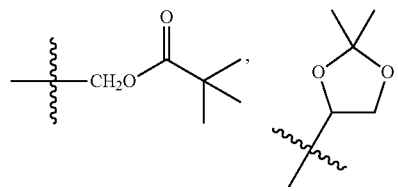

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Preferably, alkyl is a straight or branched saturated hydrocarbon radical having from 1 to 6 carbon atoms selected from methyl, ethyl, propyl or butyl; or a cyclic saturated hydrocarbon radical having from 3 to 6 carbon atoms selected from cyclopropyl or cyclohexyl, optionally substituted with cyano. Or alkyl is C$_{1-6}$alkyl. C$_{1-6}$alkyl is a straight or branched saturated hydrocarbon radical having from 1 to 6 carbon atoms such as for example methyl, ethyl, propyl, 2-methyl-ethyl, pentyl, hexyl and the like. A preferred subgroup of C$_{1-6}$alkyl is C$_{1-4}$alkyl which represents a straight or branched saturated hydrocarbon radical having from 1 to 4 carbon atoms such as for example methyl, ethyl, propyl, 2-methyl-ethyl and the like.

Preferably, aryl is naphthyl or phenyl, more preferably phenyl, each optionally substituted with one or two substituents selected from halo, for example chloro; alkyl for example methyl; or alkyloxy, for example methyloxy.

Preferably, Het is furanyl, pyridyl, pyridinyl, quinolinyl or benzofuranyl.

Preferably, halo is bromo, fluoro or chloro.

Preferably haloalkyl is trifluoromethyl.

Compounds of formula (Ia) are generally preferred.

Preferably, the present invention relates to a compound of formula (Ia) or (Ib) or any subgroup thereof as mentioned hereinbefore as a preferable embodiment, wherein R$^1$ is halo, aryl, alkyl or alkyloxy; or wherein R$^1$ is halo, cyano, alkyl or Het. More preferably, R$^1$ is halo. Most preferably, R$^1$ is bromo.

Preferably, the present invention relates to a compound of formula (Ia) or (Ib) or any subgroup thereof as mentioned hereinbefore as a preferable embodiment, wherein p is equal to zero or 1.

For compounds of formula (Ia), preferably, the present invention relates to a compound of formula (Ia) or any subgroup thereof as mentioned hereinbefore as a preferable embodiment, wherein R$^2$ is alkyloxy, aryl, aryloxy or Het, in particular alkyloxy, aryl, aryloxy or pyrrolidino. More preferably, R$^2$ is alkyloxy or aryl. Most preferably, R$^2$ is methyloxy or phenyl.

For compounds of formula (Ib), preferably, the present invention relates to a compound of formula (Ib) or any subgroup thereof as mentioned hereinbefore as a preferable embodiment, wherein R$^9$ is alkyl and R$^{10}$ is oxo.

Preferably, the present invention relates to a compound of formula (Ia) or (Ib) or any subgroup thereof as mentioned hereinbefore as a preferable embodiment, wherein R$^3$ is alkyl, arylalkyl, aryl, mono- or di-alkylaminoalkyl, or Het-alkyl for example furanyl-, pyridyl- or quinolinyl-alkyl more preferably Het-methyl most preferably furanyl-, pyridyl- or quinolinyl-methyl.

Preferably, the present invention relates to a compound of formula (Ia) or (Ib) or any subgroup thereof as mentioned hereinbefore as a preferable embodiment, wherein q is equal to 1 or 2. More preferably, q is equal to 1.

Preferably, the present invention relates to a compound of formula (Ia) or (Ib) or any subgroup thereof as mentioned hereinbefore as a preferable embodiment, wherein Het in the definition of substituent R$^4$ or R$^5$ is pyridinyl or benzofuranyl.

For compounds of Formula (Ia) or Formula (Ib) in which Z is a radical of formula (a), preferably the present invention relates to a compound of formula (Ia) or (Ib) or any subgroup thereof as mentioned hereinbefore as a preferable embodiment, wherein R$^4$ and R$^5$ each independently are hydrogen or alkyl, more preferably hydrogen, methyl or ethyl, most preferably methyl.

Preferably, the present invention relates to a compound of formula (Ia) or (Ib) or any subgroup thereof as mentioned hereinbefore as a preferable embodiment, wherein R$^4$ and R$^5$ together with the nitrogen atom to which they are attached form a radical selected from pyrrolidino, piperidino, piperazino, morpholino, 4-thiomorpholino, 2,3-dihydroisoindol-1-yl, thiazolidin-3-yl, 1,2,3,6-tetrahydropyridyl, 1-aza-4-oxacycloheptyl, 1,4-diazacycloheptyl, or 1,2,3,4-tetrahydroisoquinolin-2-yl, optionally substituted with one or two substituents, more preferably one substituent, selected from alkyl, arylalkyl, aryl, pyridyl or pyrimidinyl.

For compounds according to Formula (Ia) or Formula (Ib) in which Z is a radical of formula (b), preferably the present invention relates to a compound of formula (Ia) or (Ib) or any subgroup thereof as mentioned hereinbefore as a preferable embodiment, wherein R$^8$ is a straight or branched saturated hydrocarbon radical having from 1 to 4 carbon atoms, preferably methyl or ethyl.

Preferably, the present invention relates to a compound of formula (Ia) or (Ib) or any subgroup thereof as mentioned hereinbefore as a preferable embodiment, wherein R$^6$ is phenyl or Het for example benzofuranyl or pyridinyl, each being optionally substituted with one or two substituents independently selected from halo or alkyl.

Preferably, the present invention relates to a compound of formula (Ia) or (Ib) or any subgroup thereof as mentioned hereinbefore as a preferable embodiment, wherein R$^7$ is hydrogen or halo, for example chloro.

Preferably, the present invention relates to a compound of formula (Ia) or (Ib) or any subgroup thereof as mentioned hereinbefore as a preferable embodiment, wherein R$^9$ is alkyl, more preferable C$_{1-6}$alkyl, e.g. methyl.

Preferably, the present invention relates to a compound of formula (Ia) or (Ib) or any subgroup thereof as mentioned hereinbefore as a preferable embodiment, wherein Z is a radical of formula (a).

Preferably, the present invention relates to a compound of formula (Ia) or (Ib) or any subgroup thereof as mentioned hereinbefore as a preferable embodiment, wherein Z is a radical of formula (b).

A preferred group of compounds are those compounds according to Formula (Ia), the pharmaceutically acceptable acid or base addition salts thereof, the quaternary amines thereof, the stereochemically isomeric forms thereof, the tautomeric forms thereof, the N-oxide forms thereof or the prodrugs thereof, in which p is 0 or 1; R$^2$ is alkyloxy, aryl, aryloxy or Het; R$^3$ is alkyl, arylalkyl, aryl, mono- or di-alkylaminoalkyl, or Het-alkyl; q is equal to 1 or 2; R$^4$ and R$^5$ each independently is hydrogen; alkyl; alkyloxyalkyl; arylalkyl; Het-alkyl; mono- or dialkylaminoalkyl; Het; or aryl; or R$^4$ and R$^5$ together with the nitrogen atom to which they are attached form a radical selected from pyrrolidino, piperidino, piperazino, morpholino, 4-thiomorpholino, 2,3-dihydroisoindol-1-yl, thiazolidin-3-yl, 1,2,3,6-tetrahydropyridyl, 1-aza-4-oxacycloheptyl, 1,4-diazacycloheptyl, or 1,2,3,4-tetrahydroisoquinolin-2-yl, optionally substituted with one or two substituents, more preferably one substituent, selected from alkyl, arylalkyl, aryl, pyridyl or pyrimidinyl; R$^6$ is phenyl or Het; R$^7$ is hydrogen or halo; R$^8$ is a straight or branched saturated hydrocarbon radical having from 1 to 4 carbon atoms; R$^9$ is alkyl; R$^{10}$ is oxo.

An especially preferred group of compounds are those compounds according to Formula (Ia), the pharmaceutically acceptable acid or base addition salts thereof, the quaternary amines thereof, the stereochemically isomeric forms thereof, the tautomeric forms thereof, the N-oxide forms thereof or the pro-drugs thereof, in which p is 0 or 1; $R^1$ is halo especially bromo, or alkyl especially methyl, preferably in the 6-position; $R^2$ is alkyloxy especially methyloxy, or aryl especially phenyl; $R^3$ is aryl especially phenyl, arylalkyl especially benzyl or Het-alkyl especially quinoline-5-ylmethyl; q is 1; $R^4$ and $R^5$ each independently are alkyl especially methyl, ethyl or isopropyl or $R^4$ and $R^5$ together with the nitrogen atom to which they are attached form a 4-thiomorpholino, piperidino or piperazino radical substituted with alkyl especially methyl, at the 4-position, or with arylalkyl especially benzyl; $R^6$ is aryl especially phenyl optionally substituted with a halo especially fluoro, preferably in the 2-position, or $R^6$ is benzofuranyl; $R^7$ is hydrogen; and $R^8$ is a straight or branched saturated hydrocarbon radical having from 1 to 4 carbon atoms, especially ethyl.

Another especially preferred group of compounds on account of their activity against mycobacteria are those compounds according to Formula (Ia), the pharmaceutically acceptable acid or base addition salts thereof, the quaternary amines thereof, the stereochemically isomeric forms thereof, the tautomeric forms thereof, the N-oxide forms thereof or the pro-drugs thereof, in which p is 1; Z is a radical of formula (a); $R^1$ is bromo, or methyl, preferably in the 6-position; $R^2$ is methyloxy, or phenyl; $R^3$ is phenyl optionally substituted with methyloxy, or benzyl; q is 1; $R^4$ and $R^5$ each are methyl, ethyl or isopropyl, or $R^4$ and $R^5$ together with the nitrogen atom to which they are attached form a 4-thiomorpholino radical, a piperidino radical substituted with methyl at the 4-position or a piperazino radical substituted with benzyl at the 4-position; $R^6$ is phenyl or benzofuranyl; and $R^7$ is hydrogen.

A further especially preferred group of compounds on account of their activity against bacteria other than mycobacteria are those compounds according to Formula (Ia), the pharmaceutically acceptable acid or base addition salts thereof, the quaternary amines thereof, the stereochemically isomeric forms thereof, the tautomeric forms thereof, the N-oxide forms thereof or the pro-drugs thereof, in which p is 0 or 1; $R^1$ is bromo, or methyl, preferably in the 6-position; $R^2$ is methyloxy, or phenyl; $R^3$ is phenyl, benzyl or quinoline-5-ylmethyl; q is 1; $R^4$ and $R^5$ each are methyl or $R^4$ and $R^5$ together with the nitrogen atom to which they are attached form a piperazino radical substituted with methyl, at the 4-position; $R^6$ is phenyl optionally substituted with a fluoro, in the 2-position; $R^7$ is hydrogen; and $R^8$ is ethyl.

Most preferably, for activity against non-mycobacteria, the compound is selected from:
2-{benzyl-[(6-methyl-2-phenyl-quinolin-3-yl)-phenyl-methyl]-amino}-N-(4-methyl-piperazin-1-yl)-acetamide;
N-[(6-bromo-2-methoxy-quinolin-3-yl)-phenyl-methyl]-N',N'-dimethyl-N-phenyl-ethane-1,2-diamine;
N-benzyl-N-[(6-bromo-2-phenyl-quinolin-3-yl)-phenyl-methyl]-N',N'-dimethyl-ethane-1,2-diamine;
2-{benzyl-[(6-methyl-2-phenyl-quinolin-3-yl)-phenyl-methyl]-amino}-1-(4-methyl-piperazin-1-yl)-ethanone;
2-{[(6-bromo-2-methoxy-quinolin-3-yl)-phenyl-methyl]-quinolin-5-ylmethyl-amino}-1-(4-methyl-piperazin-1-yl)-ethanone;
2-{benzyl-[(6-bromo-2-methoxy-quinolin-3-yl)-phenyl-methyl]-amino}-1-(4-methyl-piperazin-1-yl)-ethanone;
N-benzyl-N-[(6-bromo-2-methoxy-quinolin-3-yl)-(2-fluoro-phenyl)-methyl]-N',N'-dimethyl-ethane-1,2-diamine;
{benzyl-[(6-bromo-2-methoxy-quinolin-3-yl)-phenyl-methyl]-amino}-acetic acid ethyl ester; and
2-{benzyl-[(6-methyl-2-phenyl-quinolin-3-yl)-phenyl-methyl]-amino}-1-piperidin-1-yl-ethanone;
and the pharmaceutically acceptable acid or base addition salts thereof, the quaternary amines thereof, the stereochemically isomeric forms thereof, the tautomeric forms thereof, the N-oxide forms thereof or the pro-drugs thereof.

Most preferably, for activity against mycobacteria, the compound is selected from:
2-{benzyl-[(6-methyl-2-phenyl-quinolin-3-yl)-phenyl-methyl]-amino}-1-(4-benzyl-piperazin-1-yl)-ethanone;
N-[(6-bromo-2-methoxy-quinolin-3-yl)-phenyl-methyl]-N-(2-methoxy-phenyl)-N',N'-dimethyl-ethane-1,2-diamine;
2-{benzyl-[(6-methyl-2-phenyl-quinolin-3-yl)-phenyl-methyl]-amino}-N,N-dimethyl-acetamide;
N-benzyl-N-[(6-bromo-2-phenyl-quinolin-3-yl)-phenyl-methyl]-N',N'-dimethyl-ethane-1,2-diamine;
2-{benzyl-[(6-methyl-2-phenyl-quinolin-3-yl)-phenyl-methyl]-amino}-1-(4-methyl-piperidin-1-yl)-ethanone;
2-{benzyl-[(6-methyl-2-phenyl-quinolin-3-yl)-phenyl-methyl]-amino}-N,N-diethyl-acetamide;
2-{benzyl-[(6-bromo-2-phenyl-quinolin-3-yl)-phenyl-methyl]-amino}-N,N-dimethyl-acetamide;
2-{[benzofuran-2-yl-(2-phenyl-quinolin-3-yl)-methyl]-benzyl-amino}-N-isopropyl-N-methyl-acetamide;
2-{benzyl-[(6-methyl-2-phenyl-quinolin-3-yl)-phenyl-methyl]-amino}-1-thiomorpholin-4-yl-ethanone; and
2-{benzyl-[(6-methyl-2-phenyl-quinolin-3-yl)-phenyl-methyl]-amino}-N-isopropyl-N-methyl-acetamide;
and the pharmaceutically acceptable acid or base addition salts thereof, the quaternary amines thereof, the stereochemically isomeric forms thereof, the tautomeric forms thereof, the N-oxide forms thereof or the pro-drugs thereof.

Pharmacology

The compounds according to the invention have surprisingly been shown to be suitable for the treatment of bacterial diseases including especially mycobacterial diseases, particularly those diseases caused by pathogenic mycobacteria such as *Mycobacterium tuberculosis* (including the latent and drug resistant form thereof), *M. bovis, M. avium* and *M. marinum*. The present invention thus also relates to compounds of Formula (Ia) or Formula (Ib) as defined hereinabove, the pharmaceutically acceptable acid or base addition salts thereof, the quaternary amines thereof, the stereochemically isomeric forms thereof, the tautomeric forms thereof, the N-oxide forms thereof and the pro-drugs thereof, for use as a medicine.

Further, the present invention also relates to the use of a compound of Formula (Ia) or Formula (Ib), the pharmaceutically acceptable acid or base addition salts thereof, the quaternary amines thereof, the stereochemically isomeric forms thereof, the tautomeric forms thereof, the N-oxide forms thereof and the pro-drugs thereof, as well as any of the pharmaceutical compositions thereof as described hereinafter for the manufacture of a medicament for the treatment of a bacterial disease including a mycobacterial disease.

Accordingly, in another aspect, the invention provides a method of treating a patient suffering from, or at risk of, a bacterial disease, including a mycobacterial disease, which comprises administering to the patient a therapeutically effective amount of a compound or pharmaceutical composition according to the invention.

In addition to their activity against mycobacteria, the compounds according to the invention are also active against other bacteria. In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogenes*; Bacilli, for example *Bacillus subtilis; Listeria*, for example *Listeria monocytogenes*; Haemophilus, for example *H. influenza*; Moraxella, for example *M. catarrhalis; Pseudomonas*, for example *Pseudomonas aeruginosa*; and *Escherichia*, for example *E. coli*.

Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Staphylococcus aureus*, including resistant *Staphylococcus aureus* such as for example methicillin resistant *Staphylococcus aureus* (MRSA), and *Streptococcus pneumoniae*.

In particular, the compounds of the present invention are active on those bacteria of which the viability depends on proper functioning of F1F0 ATP synthase. Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynaecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with one or more bacterial strains.

Whenever used hereinbefore or hereinafter, that the bacterial infection is other than a Mycobacterial infection it is meant that the bacterial infection is other than an infection with one or more Mycobacteria.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of formula (Ia) or Formula (Ib) are antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (Ia) or Formula (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Other Mycobacterial agents which may be combined with the compounds of formula (Ia) or (Ib) are for example rifampicin (=rifampin); isoniazid; pyrazinamide; amikacin; ethionamide; moxifloxacin; ethambutol; streptomycin; para-aminosalicylic acid; cycloserine; capreomycin; kanamycin; thioacetazone; PA-824; quinolones/fluoroquinolones such as for example ofloxacin, ciprofloxacin, sparfloxacin; macrolides such as for example clarithromycin, clofazimine, amoxycillin with clavulanic acid; rifamycins; rifabutin; rifapentine.

General Preparation

The compounds according to the invention can generally be prepared by a succession of steps, each of which is known to the skilled person.

Compounds of formula (Ia) in which Z is a radical of formula (a) in which X is —$CH_2$—, represented by formula (Ia1) below may be prepared by reacting a compound of formula (II) with a compound of formula (III) according to reaction Scheme 1 below:

Scheme 1

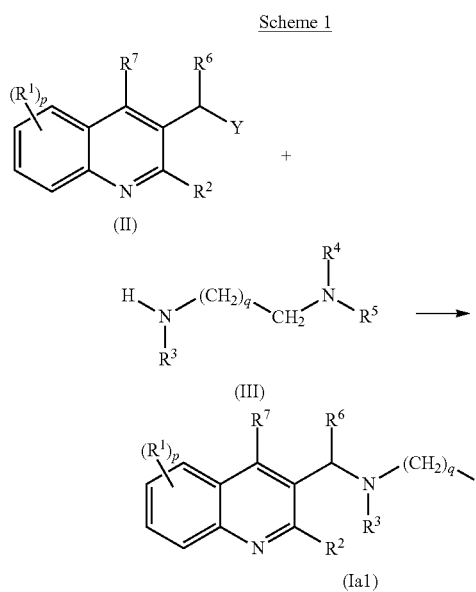

(in which Y is a leaving group such as bromo, chloro, hydroxyl, p-toluenesulphonyloxy or methanesulphonyloxy). When Y is bromo, the reaction is generally effected in the presence of a base such as potassium carbonate, sodium carbonate, $Et_3N$ and in a suitable solvent such as acetonitrile, dimethylformamide, N-methylpyrrolidone or diglyme. When Y is hydroxy the reaction is generally effected in the presence of $P(Ph)_3$ and diisopropylazodicarboxylate (DIAD) or diethylazodicarboxylate (DEAD) in a suitable solvent such as tetrahydrofuran.

Compounds of formula (Ia) in which Z is a radical of formula (b), represented by formula (Ia2) below, may be prepared by reacting a compound of formula (II) with a compound of formula (IV) according to reaction Scheme 2 below:

Scheme 2

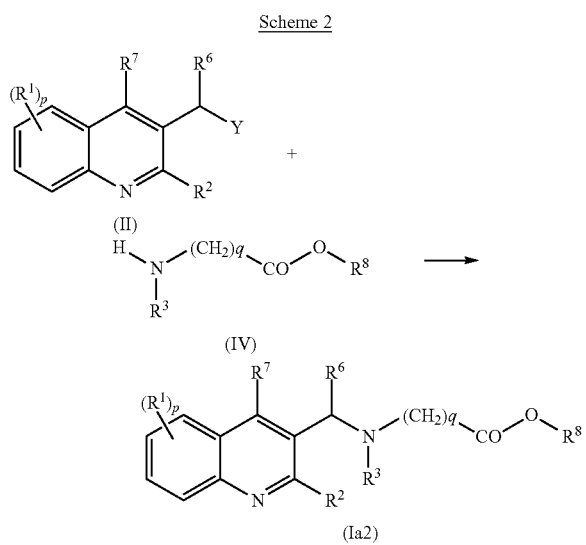

The reaction may be effected under analogous conditions to those described for the reaction in Scheme 1 above.

The compounds of formula (Ia2) may be converted into intermediate compounds of formula (V) which may be subsequently reacted with a compound of formula (VI) and converted into compounds of formula (Ia) in which Z is radical of formula (a) in which X is —CO—, represented by formula (Ia3) below, as described in reaction Scheme 3 below:

Scheme 3

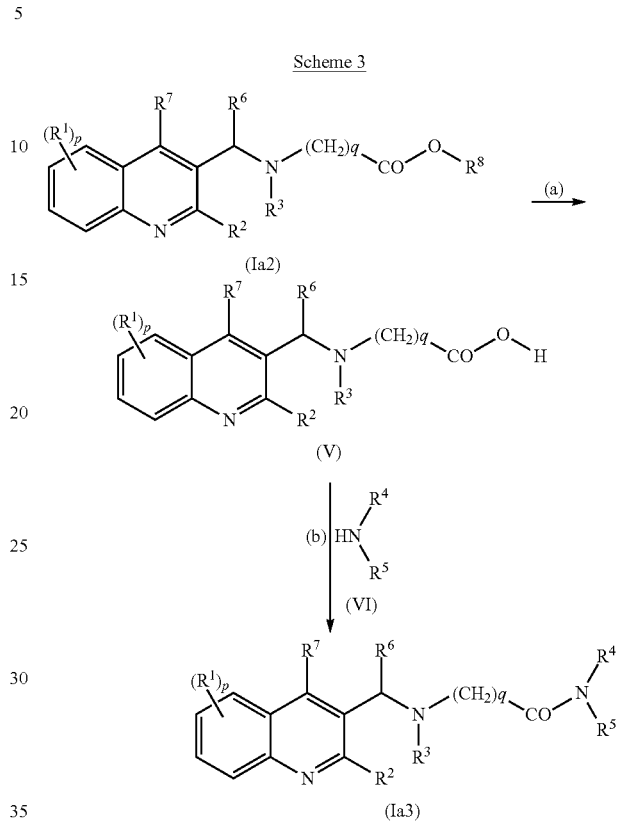

In stage (a) the compound of formula (Ia2) may be hydrolysed for example by treatment with aqueous lithium hydroxide in an organic solvent such as tetrahydrofuran. In stage (b) the intermediate compound of formula (V) is reacted with an amine compound of formula (VI) for example in the presence of N-ethyl-N'-(3-dimethylaminopropyl)carbodiimide (EDCI) and 1-hydroxybenzotriazole (HOBT) in the presence of a base such as triethylamine and in a suitable solvent such as dichloromethane and/or tetrahydrofuran.

The intermediate compound of formula (II) in which $R^6$ is aryl and Y is bromo, represented by formula (IIa1) below, may be prepared by bromination of a compound of formula (VII) in accordance with reaction Scheme 4a below:

Scheme 4a

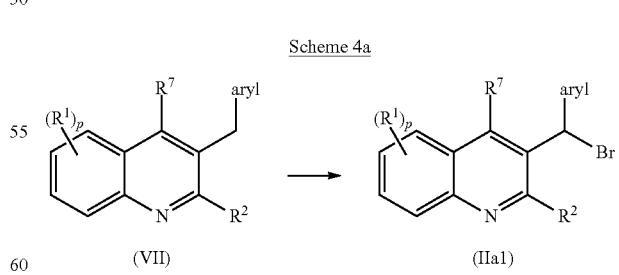

The bromination of the compound of formula (VII) may be effected for example by treatment with N-bromosuccinimide (NBS) and dibenzoyl peroxide in a suitable solvent such as carbon tetrachloride. The corresponding compound of formula (II) in which Y is chloro can be prepared in an analogous manner.

The intermediate compound of formula (II) in which $R^6$ is aryl and Y is hydroxy, represented by formula (IIa2) below, may be prepared by reaction of a compound of formula (VIIa) with a compound of formula (VIIb) in accordance with reaction Scheme 4b below:

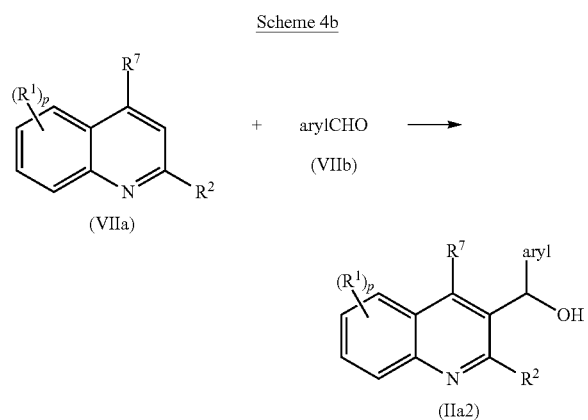

The intermediate compound of formula (II) in which $R^6$ is Het and Y is hydroxy or bromo, represented respectively by formulae (IIb1) and (II b2) below, may be prepared in accordance with reaction Scheme 5a below:

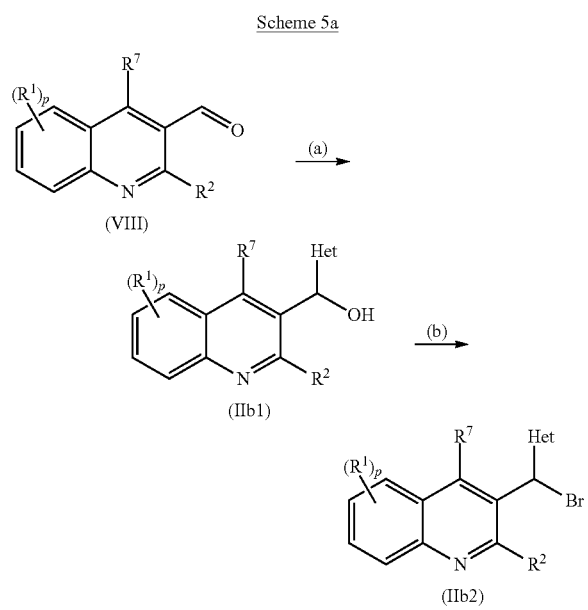

In stage (a) a compound of formula (VIII) is reacted with a compound HetH for example using n-butyllithium in a suitable solvent such as tetrahydrofuran or $Et_2O$ to effect introduction of the Het radical. In stage (b) the conversion of the hydroxy radical into the bromo radical can be effected for example by treatment of the compound of formula (IIb1) with a brominating agent such as phosphorus tribromide or aqueous hydrobromic acid, in a suitable solvent such as dichloromethane. The corresponding compound of formula (II) in which Y is chloro can be prepared in an analogous manner.

The intermediate compound of formula (II) in which $R^6$ is Het and Y is p-toluenesulphonyloxy or methanesulphonyloxy, represented below by $RSO_2O$, said intermediate compound represented by formula (IIb3) below, may be prepared in accordance with Scheme 5b below:

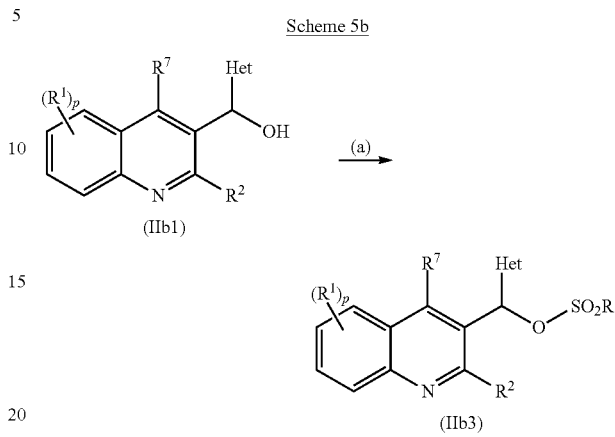

The conversion of the hydroxy radical into the mesylate or tosylate ester radical can be effected for example by treatment of compound (IIb1) with respectively methanesulphonyl chloride or p-toluenesulphonyl chloride in the presence of a base such as triethylamine and in a suitable solvent such as dichloromethane.

The intermediate compound of formula (IV) in which $R^3$ is arylmethyl or Het-methyl, represented by formula (IVa) below in which $R^{3a}$ is aryl or Het, may be prepared by reacting a compound of formula (X) with a compound of formula (XI) in accordance with reaction Scheme 6 below:

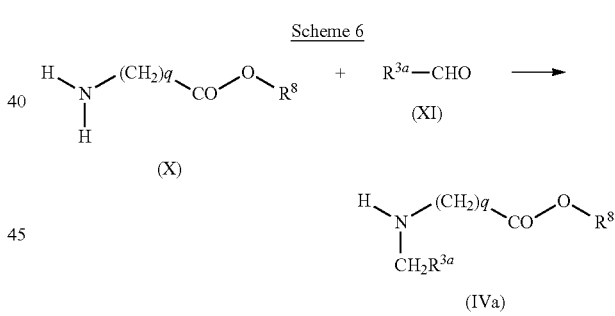

The reaction of the compound of formula (X) with the compound of formula (XI) is generally effected using sodium cyanoborohydride in the presence of an acid such as acetic acid, and in a suitable solvent such as methanol.

Alternatively the intermediate compound of formula (IV) can be prepared by reacting a compound of formula (XII) with a compound of formula (XIII) in accordance with Scheme 7 below:

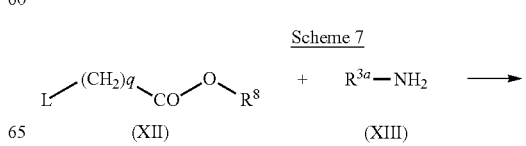

-continued

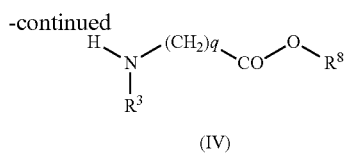

(IV)

In the compound of formula (XII) in the above Scheme L is a suitable leaving group such as chloro and the reaction is generally effected in the presence of a base such as potassium carbonate or sodium carbonate, in the presence of a suitable solvent such as acetonitrile, dimethylformamide, N-methylpyrrolidone or diglyme.

Compound of formula (Ia) in which $R^2$ is pyrrolidino, represented by formula (Ia4) below, may be prepared by reacting a compound of formula (XIV) in which $R^{2a}$ is halo, for example chloro, with pyrrolidine in accordance with Scheme 8 below:

Scheme 8

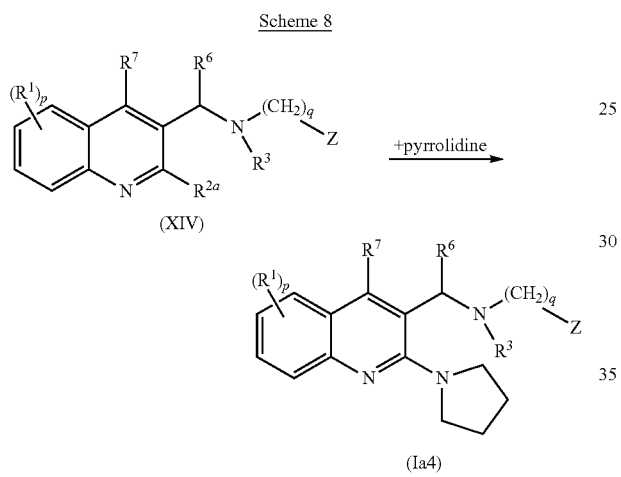

The starting materials of formula (XIV) may be prepared in an analogous manner to that described for the preparation of compounds of formula (I) as shown in Scheme 1.

Compounds of formula (I) in which $R^1$ is halo for example bromo, may be converted into corresponding compounds of formula (I) in which $R^1$ is alkyl, for example methyl, by treatment with an appropriate alkylating agent such as $CH_3B(OH)_2$ or $(CH_3)_4Sn$ in the presence of $Pd(PPh_3)_4$ in a suitable solvent such as toluene or 1,2-dimethoxyethane (DME). Similarly compounds of formula (I) in which $R^1$ is halo for example bromo may be converted into corresponding compounds of formula (I) in which $R^1$ is pyridyl by treatment with 3-(1,3,2-dioxaborinan-2-yl)-pyridine in the presence of $Pd(PPh_3)_4$ and a base such as sodium carbonate in a suitable solvent such as DME.

The compounds of formula (Ib) can be prepared in an analogous manner to that described above for the compounds of formula (Ia).

Compounds of formula (Ia) or formula (Ib) may be converted into their corresponding N-oxides in conventional manner for example by treatment with 3-chloroperbenzoic acid in a suitable solvent such dichloromethane.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of Formula (Ia) or Formula (Ib) may be separated into their isomeric forms.

The following examples illustrate the present invention without being limited thereto.

EXPERIMENTAL PART

Hereinafter, "DME" is defined as 1,2-dimethoxyethane, "NBS" is defined as N-bromosuccinimide, "DMF" is defined as N,N-dimethylformamide, "THF" is defined as tetrahydrofuran, "DIPE" is defined as diisopropylether, "BTEAC" is defined as benzyltriethylammonium chloride, "EDCI" is defined as 1-(3-dimethylaminopropyl)-3-ethylcarbodiimide-.HCl, "HOBT" is defined as 1-hydroxybenztriazole, "DIAD" is defined as diisopropylazodicarboxylate and "polymerlab NCO" is defined as methylisocyanate polystyrene.

A. Preparation of the Intermediate Compounds

Example A1 a) Preparation of Intermediate 1

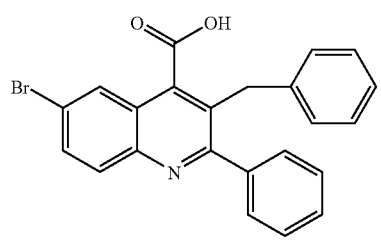

A mixture of 5-bromo-1H-indole-2,3-dione (0.066 mol) in NaOH 3N (150 ml) was stirred at 80° C. for 30 minutes, then brought to room temperature. 1,3-diphenyl-1-propanone (0.066 mol) was added and the mixture was heated to 80° C. overnight then cooled and acidified to pH 5 with acetic acid. The precipitate was filtered off, washed with $H_2O$ and diisopropyl ether and dried. Yield: 15 g of intermediate 1 (55%).

b) Preparation of Intermediate 2

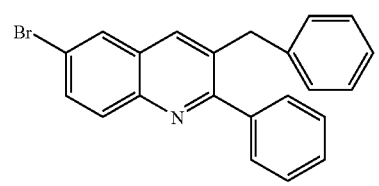

A mixture of intermediate 1 (15 g) in diphenylether (150 ml) was stirred at 300° C. overnight. The resulting mixture was purified by column chromatography over silica gel (eluc) Preparation of Intermediate 3

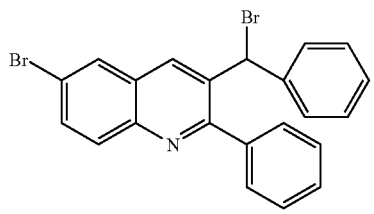

A mixture of intermediate 2 (0.0027 mol), 1-bromo-2,5-pyrrolidinedione (0.0027 mol) and dibenzoylperoxide (0.00005 mol) in CCl$_4$ (10 ml) was stirred and refluxed for 1 hour, then poured out into H$_2$O and extracted with CH$_2$Cl$_2$. The organic layer was separated, dried (MgSO$_4$), filtered, and the solvent was evaporated. Yield: 1 g of intermediate 3 (80%).

Example A2 a) Preparation of Intermediate 4

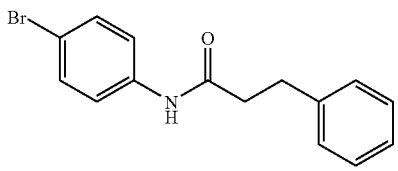

Benzene propanoyl chloride (0.488 mol) was added dropwise at room temperature to a solution of 4-bromobenzenamine (0.407 mol) in Et$_3$N (70 ml) and CH$_2$Cl$_2$ (700 ml) and the mixture was stirred at room temperature overnight. The mixture was poured out into water and concentrated NH$_4$OH, and extracted with CH$_2$Cl$_2$. The organic layer was dried (MgSO$_4$), filtered, and the solvent was evaporated. The residue was crystallized from diethyl ether. The residue (119.67 g) was taken up in CH$_2$Cl$_2$ and washed with HCl 1N. The organic layer was dried (MgSO$_4$), filtered, and the solvent was evaporated. Yield: 107.67 g of intermediate 4 (87%).

b) Preparation of Intermediate 5

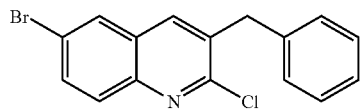

The reaction was carried out twice. POCl$_3$ (1.225 mol) was added dropwise at 10° C. to DMF (0.525 mol). Then intermediate 4 (0.175 mol) was added at room temperature. The mixture was stirred overnight at 80° C., poured out on ice and extracted with CH$_2$Cl$_2$. The organic layer was dried (MgSO$_4$), filtered, and the solvent was evaporated. The product was used without further purification. Yield: 77.62 g of intermediate 5 (67%).

c) Preparation of Intermediate 6

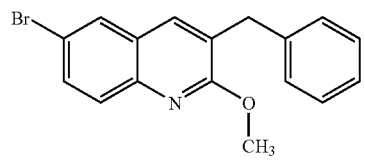

A mixture of intermediate 5 (0.233 mol) in CH$_3$ONa 30% in CH$_3$OH (222.32 ml) and CH$_3$OH (776 ml) was stirred and refluxed overnight, then poured out on ice and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/cyclohexane 20/80 and then 100/0; 20-45 μm). The pure fractions were collected and the solvent was evaporated. Yield: 25 g of intermediate 6 (33%).

d) Preparation of Intermediate 7

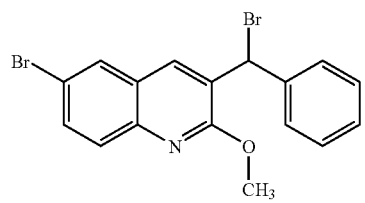

A mixture of intermediate 6 (0.03 mol), 1-bromo-2,5-pyrrolidinedione (0.03 mol) and dibenzoylperoxide (0.1 g) in CCl$_4$ (100 ml) was stirred and refluxed for 1 hour. K$_2$CO$_3$ 10% was added and the mixture was extracted with CH$_2$Cl$_2$. The organic layer was separated, dried (MgSO$_4$), filtered and the solvent was evaporated. Yield: 12.2 g of intermediate 7 (98%).

Example A3

Preparation of Intermediate 8

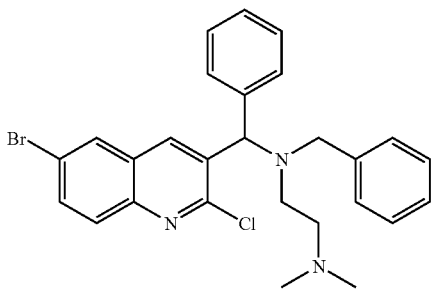

A mixture of intermediate

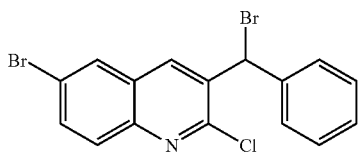

6-bromo-3-(bromo-phenyl-methyl)-2-chloro-quinoline (prepared in an analogous manner to A2.d) (0.0036 mol), N,N-dimethyl-N'-(phenylmethyl)-1,2-ethanediamine (0.0036 mol) and $K_2CO_3$ (0.0036 mol) in $CH_3CN$ (20 ml) was stirred at 80° C. for 12 hours. The solvent was evaporated. The mixture was extracted with $CH_2Cl_2/H_2O$. The organic layer was separated, dried ($MgSO_4$), filtered, and the solvent was evaporated. The residue (2.3 g) was purified by column chromatography over silica gel (eluent: $CH_2Cl_2/CH_3OH$ 98/2; 70-200 µm). The desired fraction was collected and the solvent was evaporated. Yield: 0.4 g of intermediate 8.

Example A4 a) Preparation of Intermediate 9

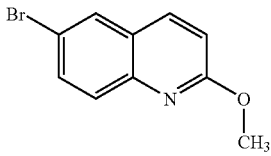

A mixture of 6-bromo-2-chloroquinoline (0.06 mol) in $CH_3ONa$ 30% $CH_3OH$ (70 ml) and $CH_3OH$ (140 ml) was stirred and refluxed overnight, poured out into $H_2O$ and extracted with $CH_2Cl_2$. The organic layer was separated, dried ($MgSO_4$), filtered and the solvent was evaporated. The residue (12.6 g) was purified by column chromatography over silica gel (eluent: $CH_2Cl_2$/cyclohexane 40/60; 15-35 µm). The desired fraction was collected and the solvent was evaporated. Yield: 7.5 g of intermediate 9.

b) Preparation of Intermediate 34

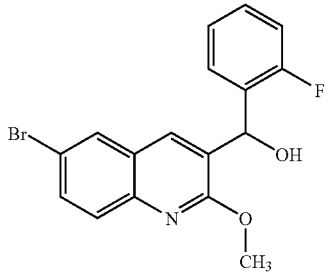

nBuLi 1.6M (0.03 mol) was added dropwise at a temperature between −20° C. and −10° C. to a solution of 2,2,6,6-tetramethylpiperidine (0.03 mol) in THF (90 ml) under $N_2$ flow. The mixture was stirred at −20° C. for 20 minutes, then cooled to −70° C. A solution of intermediate 9 (0.025 mol) in THF (39.6 ml) was added dropwise. The mixture was stirred at −70° C. for 1 hour. A solution of 2-fluorobenzaldehyde (0.03 mol) in THF (11.1 ml) was added dropwise. The mixture was stirred at −70° C. for 3 hours and 30 minutes, then brought to room temperature, stirred at room temperature overnight, poured out into $H_2O$ and extracted with EtOAc. The organic layer was washed with saturated NaCl, dried ($MgSO_4$), filtered and the solvent was evaporated. Yield: 9.96 g. This fraction was purified by column chromatography over silica gel (eluent gradient: cyclohexane/$CH_2Cl_2$ 50/50 to 100/0; 15-40 µm). Two fractions were collected and the solvent was evaporated. Yield: 2.52 g of fraction A and 0.75 g of fraction 2. A third fraction was obtained by washing the column with $CH_3OH$. The solvent was evaporated. Yield: 4.10 g of intermediate 34 (45%).

Example A5 a) Preparation of Intermediate 10

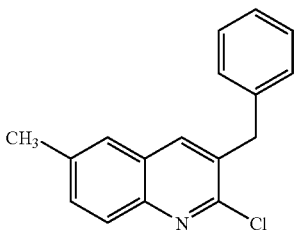

$POCl_3$ (327 ml) was added slowly at 5° C. to DMF (120 ml). After complete addition, N-(4-methylphenyl)benzenepropanamide (0.501 mol) was added. The mixture was stirred at 80° C. overnight, then brought to room temperature and poured out on ice. EtOAc was added. The mixture was stirred for 1 hour, while ice was added and then extracted with EtOAc. The organic layer was separated, washed with $H_2O$, dried ($MgSO_4$), filtered and the solvent was evaporated. Yield: 182.2 g of intermediate 10.

b) Preparation of Intermediate 11

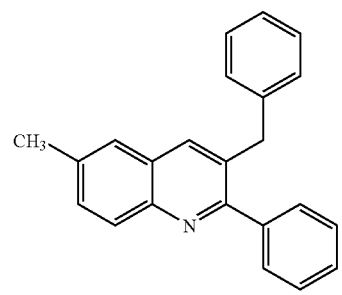

A mixture of intermediate 10 (0.0112 mol), phenylboronic acid (0.034 mol), $Pd(PPh_3)_4$ (0.0011 mol) and $Na_2CO_3$ 2M (0.056 mol) in DME (50 ml) was stirred at 90° C., poured out into $H_2O$ and extracted with $CH_2Cl_2$. The organic layer was separated, dried ($MgSO_4$), filtered, and the solvent was evaporated. The residue (5 g) was crystallized from DIPE. The precipitate was filtered off and dried. Yield: 1 g (29%). This fraction was purified by column chromatography over silica gel (eluent: cyclohexane/EtOAc 90/10; 15-0 µm). The pure fractions were collected and the solvent was evaporated. Yield: 2 g of intermediate 11 (58%).

c) Preparation of Intermediate 12

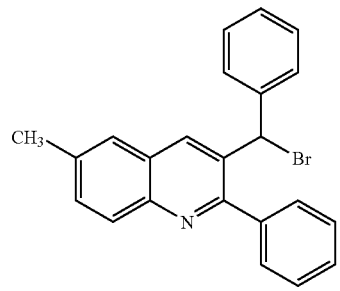

A mixture of intermediate 11 (0.0088 mol) and NBS (0.0098 mol) in 1,2-dichloroethane (50 ml) was stirred and refluxed for 3 hours, poured out into H$_2$O and extracted with CH$_2$Cl$_2$. The organic layer was separated, dried (MgSO$_4$), filtered, and the solvent was evaporated. Yield: 3.6 g of intermediate 12.

Example A6 a) Preparation of Intermediate 13

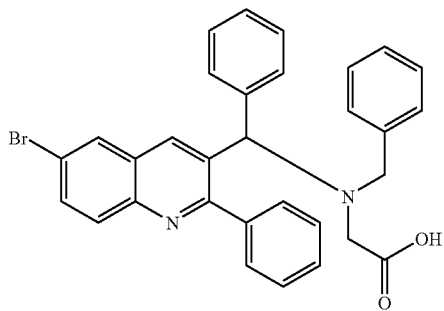

LiOH, H$_2$O (0.0035 mol) was added to a mixture of final compound 146 (prepared according to B1.a) (0.0018 mol) in THF (10 ml) and H$_2$O (10 ml). The mixture was stirred at 60° C. overnight. THF was evaporated. HCl 3N was added. The precipitate was filtered off and dried. Yield: 1 g of intermediate 13 (100%).

b) Preparation of Intermediate 14

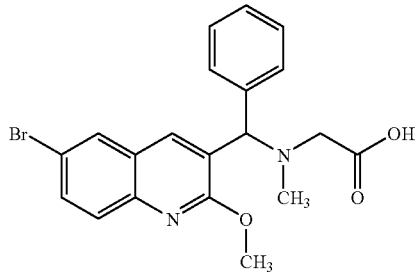

Intermediate 14 was prepared in an analogous manner to intermediate 13 but starting from final compound 131 (prepared according to B2.a) Yield: intermediate 14 (86%).

c) Preparation of Intermediate 15

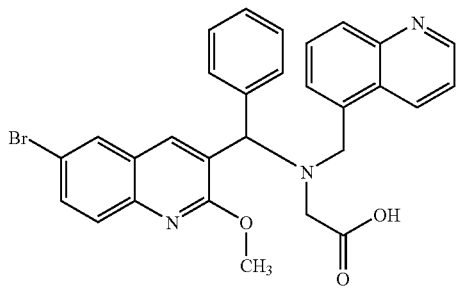

A mixture of final compound 145 (prepared according to B2.c) (0.0008 mol) and LiOH, H$_2$O (0.0026 mol) in THF (8 ml) and H$_2$O (2 ml) was stirred at room temperature for 12 hours, then stirred at 60° C. for 12 hours, poured out into H$_2$O. HCl 5N was added till pH was set to 5. The mixture was extracted with CH$_2$Cl$_2$. The organic layer was separated, dried (MgSO$_4$), filtered, and the solvent was evaporated. Yield: 0.45 g of intermediate 15 (97%).

d) Preparation of Intermediate 16

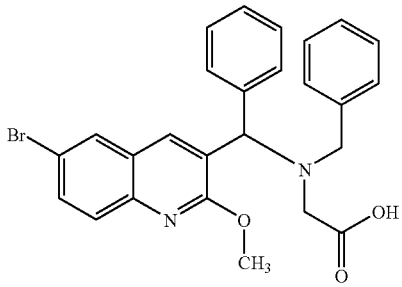

A mixture of final compound 137 (prepared according to B2.b) (0.0069 mol) and LiOH, H$_2$O (0.0143 mol) in THF (20 ml) and H₂O (20 ml) was stirred at room temperature for 12 hours, then stirred at 60° C. for 24 hours. THF was evaporated. The residue was taken up in H₂O/HCl 3N. The mixture was extracted with CH₂Cl₂. The organic layer was separated, dried (MgSO₄), filtered, and the solvent was evaporated. Yield: 3 g of intermediate 16 (56%).

e) Preparation of Intermediate 17

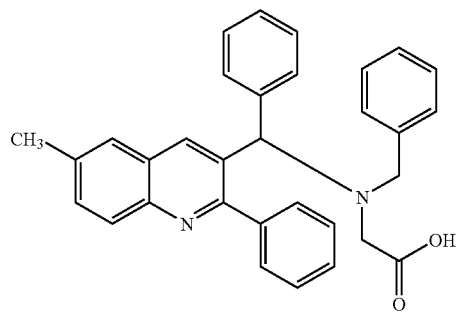

A mixture of final compound 150 (prepared according to B1.b) (0.0007 mol) and LiOH, H₂O (0.0023 mol) in THF (10 ml) and H₂O (10 ml) was stirred at room temperature for 12 hours, poured out into H₂O. HCl 3N was added. The mixture was extracted with CH₂Cl₂. The organic layer was separated, dried (MgSO₄), filtered, and the solvent was evaporated. Yield: 0.3 g of intermediate 17.

f) Preparation of Intermediate 18

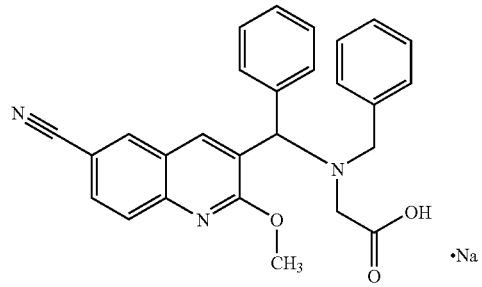

A mixture of final compound 151 (prepared according to B2.d) (0.0038 mol) and LiOH, H₂O (0.0077 mol) in H₂O (20 ml) and THF (20 ml) was stirred at room temperature for 4 days. H₂O and EtOAc were added. NaOH 3N was added. The organic layer was washed with saturated NaCl, dried (MgSO₄), filtered and the solvent was evaporated. Yield: 1.6 g of intermediate 18 (90%).

g) Preparation of Intermediate 37

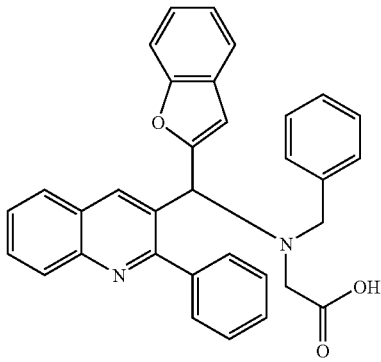

A mixture of final compound 130 (prepared according to B2.h) (0.0015 mol) and LiOH, H₂O (0.0045 mol) in THF (8 ml) and H₂O (8 ml) was stirred at 65° C. for 24 hours, then cooled to room temperature. HCl 3N was added. The mixture was evaporated till dryness. Yield: 0.85 g of intermediate 37 (100%).

Example A7 a) Preparation of Intermediate 19

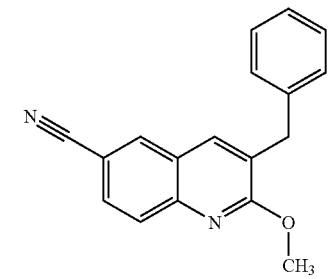

A mixture of intermediate 6 (prepared according to A2.c) (0.0076 mol) and CuCN (0.028 mol) in DMF (25 ml) was stirred and refluxed for 16 hours, then cooled to room temperature and poured out into ice water. The precipitate was filtered, taken up in H₂O/ethylene diamine and extracted with CH₂Cl₂. The organic layer was washed with satured NaCl, dried (MgSO₄), filtered, and the solvent was evaporated. The mixture was filtered over silica gel (eluent: CH₂Cl₂). The filtrate was evaporated till dryness. Yield: 1.1 g of intermediate 19 (53%).

b) Preparation of Intermediate 20

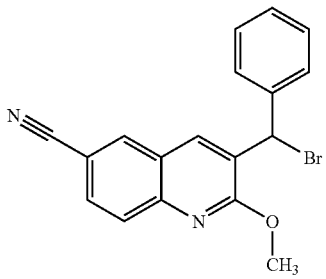

A mixture of intermediate 19 (0.0066 mol), NBS (0.0066 mol) and dibenzoylperoxide (0.0003 mol) in 1,2-dichloroethane (30 ml) was stirred at 80° C. for 3 hours, then cooled to room temperature. H₂O and CH₂Cl₂ were added. The organic layer was washed with H₂O, dried (MgSO₄), filtered and the solvent was evaporated. The residue (3.5 g) was purified by column chromatography over silica gel (eluent: cyclohexane/EtOAc 92/8; 15-40 μm). The pure fractions were collected and the solvent was evaporated. Yield: 1.9 g of intermediate 20 (81%).

Example A8 a) Preparation of Intermediate 21

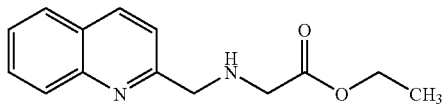

A mixture of 2-quinolinecarboxaldehyde (0.0019 mol), ethyl ester glycine hydrochloride (0.002 mol) and NaBH₃CN (0.0028 mol) in CH₃OH (1 ml) and CH₃COOH (20 ml) was stirred at room temperature for 3 hours, poured out into H₂O and K₂CO₃ 10% and extracted with CH₂Cl₂/CH₃OH. The organic layer was separated, dried (MgSO₄), filtered, and the solvent was evaporated. The residue was purified by column chromatography over silica gel (eluent: CH₂Cl₂/CH₃OH/NH₄OH 98/2/0.1; 15-40 μm). Two fractions were collected and the solvent was evaporated. Yield: 1.7 g of intermediate 21 (37%).

b) Preparation of Intermediate 27

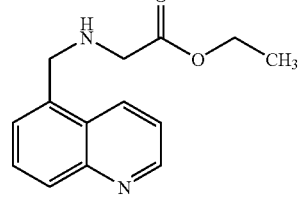

Sodium cyanoborohydride (0.0334 mol) was added portion wise to a mixture of 5-quinolinecarboxaldehyde (0.0223 mol), glycine ethyl ester hydrochloride (0.0245 mol) and acetic acid (0.5 ml) in methanol (80 ml) at 0° C. The mixture was stirred for 4 hours at room temperature then poured into K₂CO₃ 10% and extracted with CH₂Cl₂. The organic layer was dried over magnesium sulfate, filtered, and the solvent was evaporated. The residue was purified by column chromatography over silica gel (eluent: CH₂Cl₂/MeOH/NH4OH: 97.5/2.5/0.1). The pure fractions were collected and the solvent was evaporated. Yield: 2.3 g of intermediate 27 (43%).

Example A9 a) Preparation of Intermediate 22

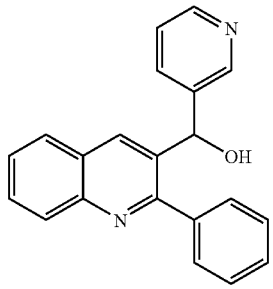

nBuLi 1.6M in hexane (0.0103 mol) was added at −70° C. to a solution of 3-bromopyridine (0.0103 mol) in diethyl ether (20 ml) under N₂ flow. The mixture was brought to 45° C., then cooled again to −70° C. A solution of 2-phenyl-3-quinoline-carboxaldehyde (0.0008 mol) in THF (20 ml) was added. The mixture was stirred from −70° C. to room temperature for 2 hours. H₂O was added. The mixture was extracted with EtOAc. The organic layer was washed with saturated NaCl, dried (MgSO₄), filtered and the solvent was evaporated. The residue was taken up in diethyl ether. The mixture was filtered, washed with diethyl ether and dried at 50° C. under vacuo. Yield: 2.1 g of intermediate 22 (79%).

b) Preparation of Intermediate 23

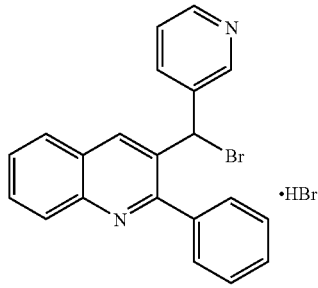

A mixture of intermediate 22 (0.0046 mol) in PBr₃ (3 ml) and toluene (45 ml) was stirred and refluxed for 1 hour and 30 minutes, then cooled to room temperature. The precipitate was filtered, washed with diethyl ether and dried at 60° C. under vacuo. Yield: 2.4 g of intermediate 23 (>100%) (melting point: 161° C.).

Example A10 a) Preparation of Intermediate 24

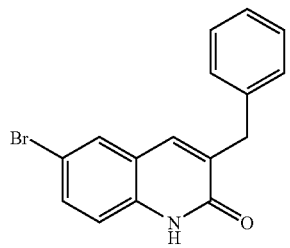

A mixture of intermediate 5 (prepared according to A2.b) (0.009 mol) in HCl (6N) (50 ml) was stirred and refluxed overnight. The precipitate was filtered, washed with $H_2O$, then with DIPE and dried. Yield: 2.8 g of intermediate 24.

b) Preparation of Intermediate 25

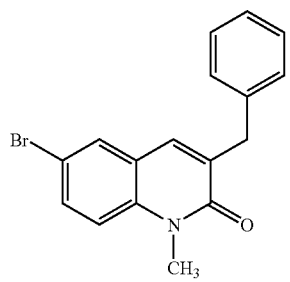

A mixture of intermediate 24 (0.0089 mol), $ICH_3$ (0.026 mol) and BTEAC (0.0044 mol) in NaOH (40 ml) and THF (30 ml) was stirred at room temperature overnight. $H_2O$ was added. The mixture was extracted with EtOAc. The organic layer was separated, dried ($MgSO_4$), filtered, and the solvent was evaporated. Yield: 1.5 g of intermediate 25 (79%).

c) Preparation of Intermediate 26

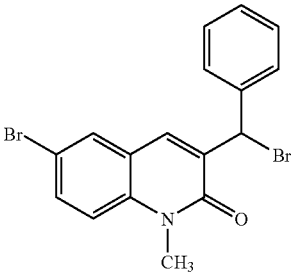

A mixture of intermediate 25 (0.0043 mol) and NBS (0.0048 mol) in 1,2-dichloro-ethane (25 ml) was stirred and refluxed for 3 hours, poured out into $H_2O$. The organic layer was separated, dried ($MgSO_4$), filtered, and the solvent was evaporated.

Yield: 2 g of intermediate 26.

Example A11 a) Preparation of Intermediate 28

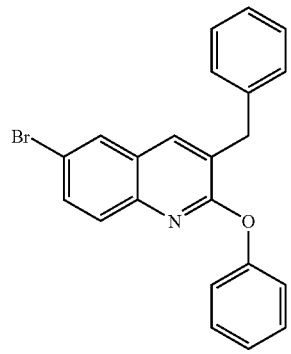

Phenol (0.066 mol) was added portion wise to a mixture of NaH 60% (0.069 mol) in 1,4-dioxane (200 ml) and DMF (80 ml) then intermediate 5 (prepared according to A2.b) (0.033 mol) was added and the suspension was heated under reflux for 20 hours. The mixture was cooled and poured into $K_2CO_3$ 10% and extracted with $CH_2Cl_2$. The organic layer was dried over magnesium sulfate, filtered, and the solvent was evaporated. The residue was purified by column chromatography over silica gel (eluent: cyclohexane/$CH_2Cl_2$: 70/30). The pure fractions were collected and the solvent was evaporated. Yield: 7.3 g of intermediate 28 (57%) (melting point: 111° C.).

b) Preparation of Intermediate 29

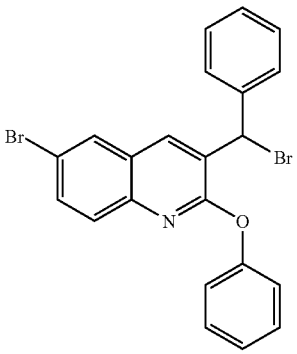

A mixture of intermediate 28 (0.0026 mol), NBS (0.0028 mol) and dibenzoylperoxide (0.00005 mol) was stirred at 80° C. for 3 hours, poured out into $H_2O$ and extracted with $CH_2Cl_2$. The organic layer was separated, dried ($MgSO_4$), filtered, and the solvent was evaporated. Yield: 1.3 g of intermediate 29 (100%) (melting point: 110° C.).

Example A12

Preparation of Intermediate 30

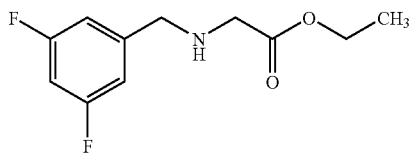

A mixture of 3,5-difluorobenzylamine (4.2 mmol), ethylchloroacetate (4.2 mmol) and potassium carbonate (4.2 mmol) in acetonitrile (7 ml) was stirred at 80° C. for 18 hours. The mixture was cooled and poured into water and extracted with $CH_2Cl_2$. The organic layer was dried over magnesium sulfate, filtered, and the solvent was evaporated. Yield: 0.58 g of intermediate 30 (60%).

Example A13 a) Preparation of Intermediate 31

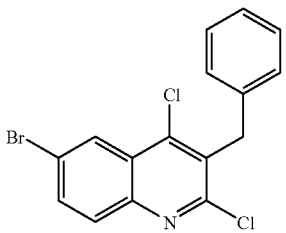

A mixture of 4-bromoaniline (0.011 mol), benzylmalonic acid (0.011 mol) and phosphorous oxychloride (10 ml) was heated for 5 hours at 80° C. then evaporated till dryness. The residue was taken up in water and $CH_2Cl_2$, basified, extracted with $CH_2Cl_2$, dried over magnesium sulfate, filtered and the solvent was evaporated. Yield: 2.48 g of intermediate 31 (62%).

b) Preparation of Intermediate 32

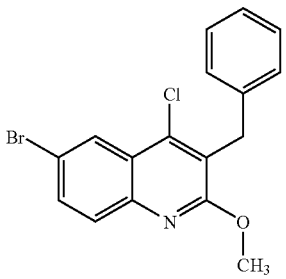

A mixture of intermediate 31 (0.011 mol) and sodium methoxide (30% in MeOH, 0.011 mol) in MeOH was heated under reflux for 3 hours then cooled to room temperature and poured into ice/water. The precipitate was filtered off, dried and purified by column chromatography over silica gel (eluent: cyclohexane/$CH_2Cl_2$: 70/30). The pure fractions were collected and the solvent was evaporated. Yield: 1.6 g of intermediate 32 (40%).

c) Preparation of Intermediate 33

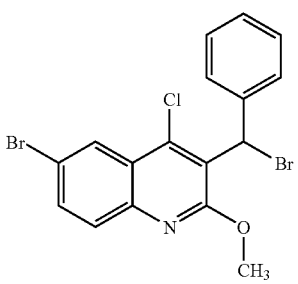

A mixture of intermediate 32 (0.0053 mol), NBS (0.0053 mol) and dibenzoylperoxide (0.0002 mol) in trifluorotoluene (31 ml) was stirred at 80° C. for 5 hours, then cooled to room temperature. $H_2O$ and $CH_2Cl_2$ were added. The organic layer was washed with $H_2O$, dried ($MgSO_4$), filtered and the solvent was evaporated. The residue (2.68 g) was crystallized from diethyl ether. The precipitate was filtered off and dried. Yield: 2.4 g of intermediate 33 (85%) (melting point: 117° C.).

Example A14 a) Preparation of Intermediate 35

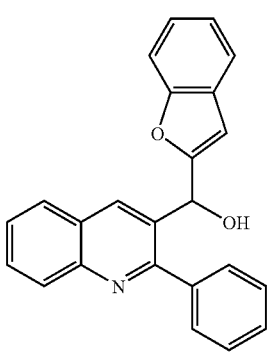

nBuLi 1.6M in hexane (0.0257 mol) was added at −70° C. to a solution of benzofuran (0.0257 mol) in THF (30 ml) under $N_2$ flow. The mixture was stirred at −70° C. for 3 hours. A solution of 2-phenyl-quinoline-3-carbaldehyde (prepared according to the teachings in US Pat. Appl. publ. (2004) 2004009976 of which the content is included herein) (0.0129 mol) in THF (30 ml) was added. The mixture was stirred at −70° C. for 3 hours, then poured out on ice at −20° C. and extracted with EtOAc. The organic layer was washed with a saturated aqueous NaCl solution, dried ($MgSO_4$), filtered and the solvent was evaporated. The residue was crystallized from diethyl ether. The precipitate was filtered off and dried. Yield: 3.75 g of intermediate 35 (83%) (melting point: 184° C.).

b) Preparation of Intermediate 36

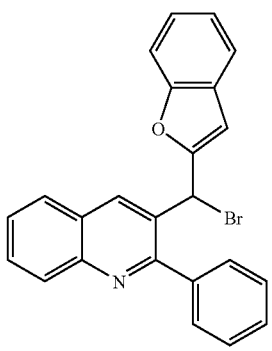

PBr$_3$ (0.0006 mol) was added dropwise at room temperature to a solution of intermediate 35 (0.0005 mol) in CH$_2$Cl$_2$ (5 ml). The mixture was stirred at room temperature for 30 minutes then evaporated till dryness. Yield: intermediate 36.

B. Preparation of the Final Compounds

Example B1 a) Preparation of Compound 146

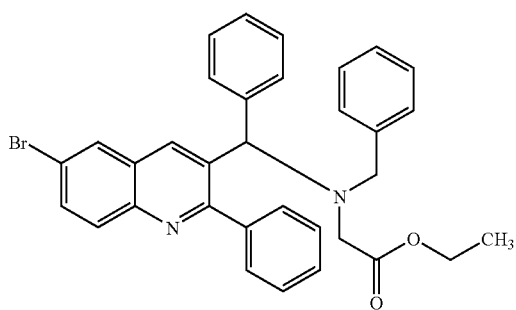

A mixture of intermediate 3 (prepared according to A1.c) (0.0004 mol), N-(phenylmethyl)glycine ethyl ester (0.0008 mol) and K$_2$CO$_3$ (0.0013 mol) in CH$_3$CN (6 ml) was stirred at 80° C. overnight. H$_2$O was added. The mixture was extracted with CH$_2$Cl$_2$. The organic layer was separated, dried (MgSO$_4$), filtered, and the solvent was evaporated. The residue (0.3 g) was purified by column chromatography over kromasil (eluent: cyclohexane/EtOAc 90/10; 10 μm). The pure fractions were collected and the solvent was evaporated. Yield: 0.165 g of final compound 146 (66%).

b) Preparation of Compound 150

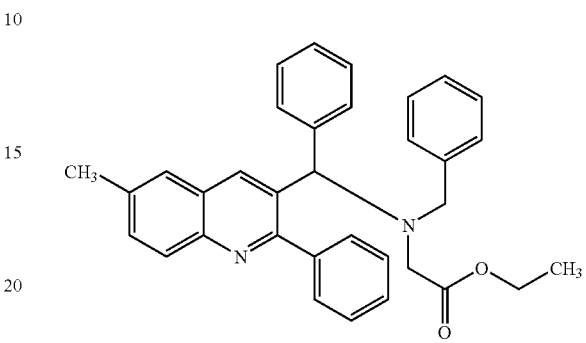

A mixture of final compound 146 (prepared according to B1.a) (0.0007 mol), tetrakis(triphenylphosphine) palladium (0.00007 mol) and (CH$_3$)$_4$Sn (0.0014 mol) in toluene (8 ml) was stirred and refluxed for 2 hours, poured out into H$_2$O and extracted with CH$_2$Cl$_2$. The organic layer was separated, dried (MgSO$_4$), filtered, and the solvent was evaporated. The residue was purified by column chromatography over silica gel (eluent: cyclohexane/EtOAc 90/10; 15-40 μm). The pure fractions were collected and the solvent was evaporated. Yield: 0.109 g of final compound 150 (31%).

c) Preparation of Compound 152

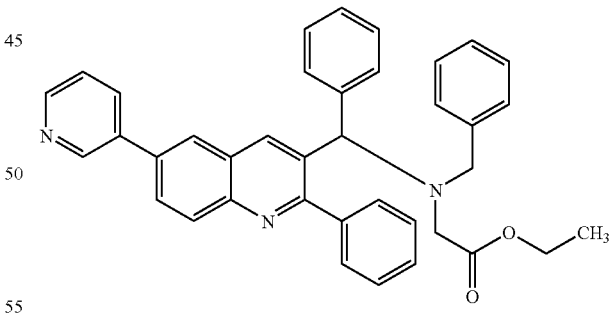

A mixture of final compound 146 (prepared according to B1.a) (0.53 mmol), Pd(PPh$_3$)$_4$ (0.053 mmol), pyridine boronic acid-1,3-propanediol cyclic ester (0.0016 mol) and aqueous sodium carbonate (2M, 0.0027 mol) in dimethylglycol (7 ml) was stirred at 90° C. for 2 hours then poured into water, and extracted with CH$_2$Cl$_2$. The organic layer was separated, dried over magnesium sulfate, filtered, and the solvent was evaporated. The residue was purified by column chromatography over silica gel (eluent: CH$_2$Cl$_2$/MeOH:

95/5). The pure fractions were collected and the solvent was evaporated. Yield: 62 mg of final compound 152 (21%).

Example B2 a) Preparation of Compound 131

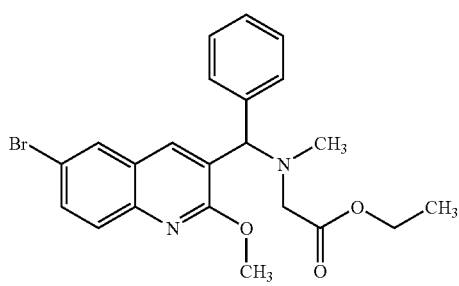

A mixture of intermediate 7 (prepared according to A2.d) (0.24 mmol), sarcosine ethyl ester hydrochloride (0.24 mmol) and $K_2CO_3$ (0.24 mmol) in $CH_3CN$ (5 ml) was stirred at 80° C. for 18 hours. The mixture was cooled and poured into water and extracted with $CH_2Cl_2$. The organic layer was dried over $MgSO_4$, filtered, and the solvent was evaporated. The residue was crystallized from diisopropyl ether. The precipitate was filtered off and dried. Yield: final compound 137 (100%).

b) Preparation of Compound 137

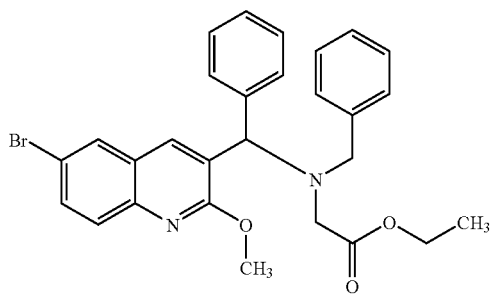

A mixture of intermediate 7 (prepared according to A2.d) (0.004 mol), N-(phenyl-methyl)glycine ethyl ester (0.0009 mol) and $K_2CO_3$ (0.0014 mol) in $CH_3CN$ (8 ml) was stirred at 80° C. overnight, poured out into $H_2O$ and extracted with $CH_2Cl_2$. The organic layer was separated, dried ($MgSO_4$), filtered, and the solvent was evaporated. The residue (0.3 g) was purified by column chromatography over silica gel (eluent: cyclohexane/EtOAc 90/10; 15-40 μm). The pure fractions were collected and the solvent was evaporated. Yield: 0.054 g of final compound 137 (21%).

c) Preparation of Compound 145

A mixture of intermediate 7 (prepared according A2.d) (0.0098 mol), intermediate 27 (prepared according to A8.b) (0.0098 mol) and $K_2CO_3$ (0.0108 mol) in $CH_3CN$ (80 ml) was stirred at 80° C. for 12 hours. The solvent was evaporated. The mixture was extracted with $CH_2Cl_2/H_2O$. The organic layer was separated, dried ($MgSO_4$), filtered, and the solvent was evaporated. The residue (5.4 g) was purified twice by column chromatography over silica gel (eluent gradient: $CH_2Cl_2$/ $CH_3OH$ 98/2 to 99/1; 15-40 μm). The pure fractions were collected and the solvent was evaporated. Yield: 0.66 g of final compound 145 (12%) (melting point: 96° C.).

d) Preparation of Compound 151

A mixture of intermediate 20 (prepared according to A7.b) (0.0053 mol), N-(phenyl-methyl)glycine ethyl ester (0.008 mol) and $K_2CO_3$ (0.008 mol) in $CH_3CN$ (20 ml) was stirred and refluxed for 18 hours, then cooled to room temperature and poured out into $H_2O$ and EtOAc. The organic layer was washed with saturated NaCl, dried ($MgSO_4$), filtered and the solvent was evaporated. The residue (3 g) was crystallized from diethyl ether. The precipitate was filtered off and dried. Yield: 1.85 g of final compound 151 (74%) (melting point: 148° C.).

e) Preparation of Compound 129

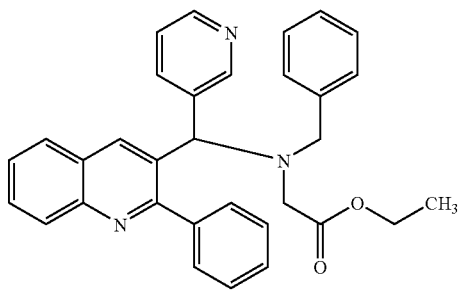

A solution of intermediate 23 (prepared according to A9.b) (0.0037 mol) in N-(phenylmethyl)glycine ethyl ester (7 ml) was stirred at 125° C. for 6 hours, then cooled to room temperature, poured out into H₂O and extracted with EtOAc. The organic layer was washed with H₂O, then with a saturated aqueous NaCl solution, dried (MgSO₄), filtered and the solvent was evaporated. Yield: 0.4 g. This fraction was purified by column chromatography over silica gel (eluent: cyclohexane/EtOAc 60/40; 15-40 μm). Two fractions were collected and the solvent was evaporated. Yield: 2.65 g of fraction 1 and 0.35 g of fraction 2 (19%). Fraction 1 was taken up in CH₂Cl₂/polymerlab NCO. The mixture was stirred at room temperature for 2 hours, then filtered. The filtrate was evaporated. Yield: 0.32 g of final compound 129 (18%).

f) Preparation of Compound 153

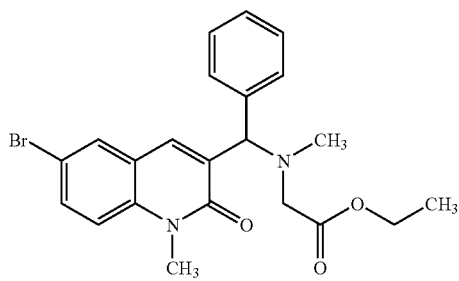

A mixture of intermediate 26 (prepared according to A10.c) (0.0012 mol), N-methylglycine ethyl ester hydrochloride (0.0019 mol) and K₂CO₃ (0.0024 mol) in CH₃CN (15 ml) was stirred at 80° C. for 6 hours. The solvent was evaporated till dryness. The residue was taken up in H₂O and CH₂Cl₂.

The organic layer was separated, dried (MgSO₄), filtered and the solvent was evaporated. Yield: 0.46 g of final compound 153.

g) Preparation of Compound 132

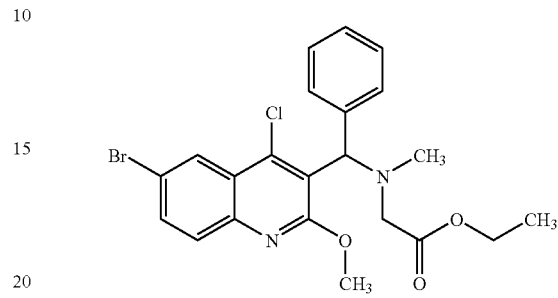

A mixture of intermediate 33 ((prepared according to A13.c) (0.0027 mol), N-methylglycine ethyl ester hydrochloride (0.0027 mol) and K₂CO₃ (0.004 mol) in CH₃CN (12 ml) was stirred and refluxed for 23 hours. N-methylglycine ethyl ester hydrochloride (1 equivalent) then K₂CO₃ (1 equivalent) were added. The mixture was stirred and refluxed for 24 hours, then cooled to room temperature, poured out into H₂O and EtOAc. The organic layer was washed with saturated NaCl, dried (MgSO₄), filtered and the solvent was evaporated. The residue (1.15 g) was purified by column chromatography over silica gel (eluent: cyclohexane/EtOAc 95/5; 15-40 μm). The desired fraction was collected and the solvent was evaporated. Yield: 0.68 g of final compound 132 (52%).

h) Preparation of Compound 130

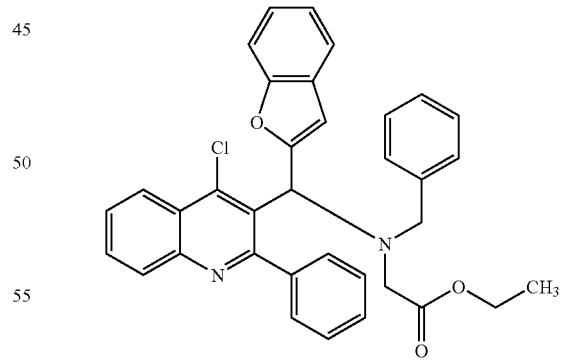

A mixture of intermediate 36 (prepared according to A14.b) (0.0056 mol), N-(phenyl-methyl)glycine ethyl ester (0.0171 mol) and K₂CO₃ (0.0171 mol) in CH₃CN (50 ml) was stirred and refluxed for 18 hours, poured out into H₂O and extracted with CH₂Cl₂. The organic layer was washed with saturated NaCl, dried (MgSO₄), filtered and the solvent was evaporated. The residue (5 g) was purified by column chromatography over silica gel (eluent: cyclohexane/EtOAc 90/10). The pure fractions were collected and the solvent was evaporated. Yield: 0.79 g of final compound 130 (27%).

i) Preparation of Compound 143

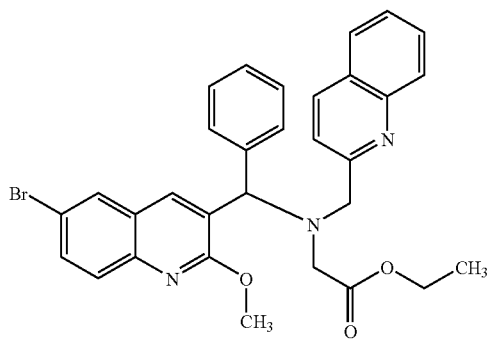

Final compound 143 was prepared in an analogous manner to B2.c starting from intermediate 21.

j) Preparation of Compound 148

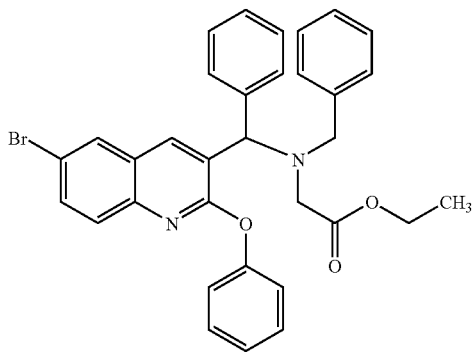

Final compound 148 was prepared in an analogous manner to B2.c starting from intermediate 29.

k) Preparation of Compound 141

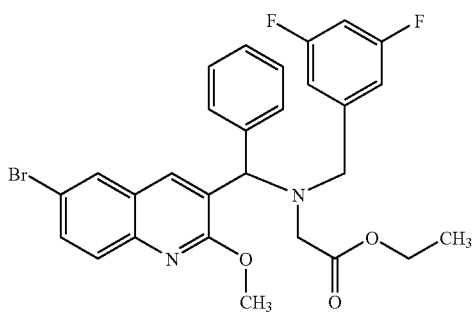

Final compound 141 was prepared in an analogous manner to B2.c starting from intermediate 30.

Example B3 a) Preparation of Compound 53

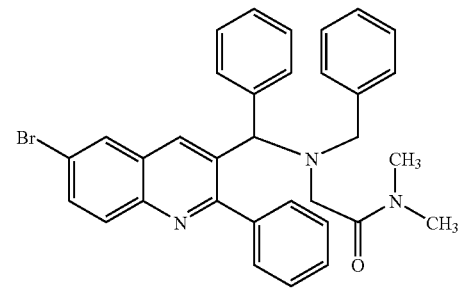

A mixture of intermediate 13 (prepared according to A6.a) (0.0003 mol), dimethylamine (0.0005 mol), EDCI (0.0005 mol), HOBT (0.0005 mol) and Et$_3$N (0.0005 mol) in CH$_2$Cl$_2$/THF (8 ml) was stirred at room temperature for 3 hours, poured out into H$_2$O and extracted with CH$_2$Cl$_2$. The organic layer was separated, dried (MgSO$_4$), filtered and the solvent was evaporated. The residue (0.2 g) was crystallized from DIPE. The precipitate was filtered off and dried. Yield: 0.053 g of final compound 53 (melting point: 110° C.).

b) Preparation of Compound 30

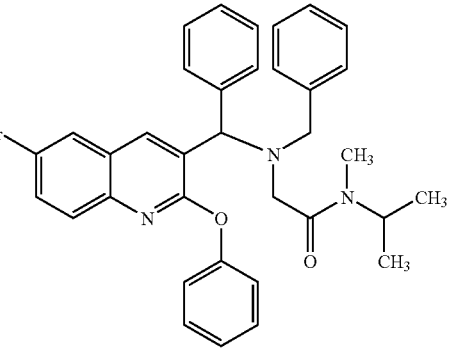

A mixture of intermediate

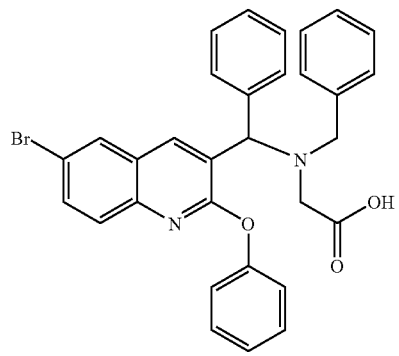

({benzyl-[(6-bromo-2-phenoxy-quinolin-3-yl)-phenyl-methyl]-amino}-acetic acid) (prepared in an analogous manner to A6.c) (0.0002 mol), N-methyl-2-propanamine hydrochloride (0.0003 mol), EDCI (0.0004 mol) and HOBT (0.0004 mol) in CH$_2$Cl$_2$ (3 ml) and THF (3 ml) was stirred at room temperature for 12 hours, then poured out into H$_2$O and CH$_2$Cl$_2$. The organic layer was separated, dried (MgSO$_4$), filtered and the solvent was evaporated. The residue (0.25 g) was purified by column chromatography over kromasil (15 μm). The pure fractions were collected and the solvent was evaporated. Yield: final compound 30 (37%).

c) Preparation of Compound 3

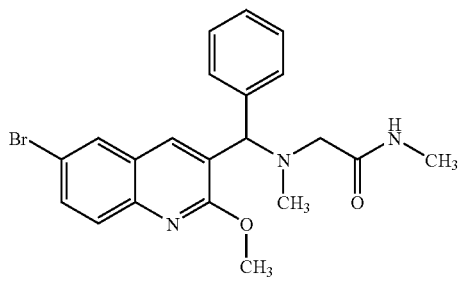

A mixture of intermediate 14 (prepared according to A6.b) (0.0002 mol), methylamine hydrochloride (0.0002 mol), EDCI (0.0003 mol) and HOBT (0.0003 mol) in CH$_2$Cl$_2$ (2 ml), THF (2 ml) and triethylamine (0.1 ml) was stirred at room temperature for 12 hours, then poured out into H$_2$O and extracted with CH$_2$Cl$_2$. The organic layer was separated, dried (MgSO$_4$), filtered, and the solvent was evaporated. The residue (0.15 g) was purified by column chromatography over kromasil (eluent: CH$_2$Cl$_2$ 100 to CH$_2$Cl$_2$/CH$_3$OH 90/10; 5 μm). The pure fractions were collected and the solvent was evaporated. Yield: 0.063 g of final compound 3 (62%) (melting point: 190° C.).

d) Preparation of Compound 41

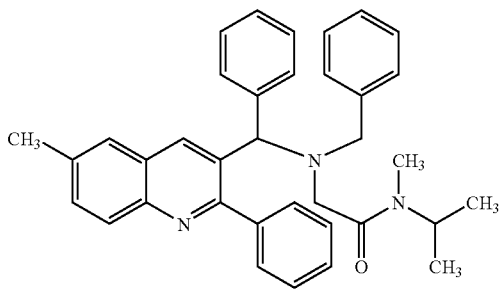

A mixture of intermediate 17 (prepared according to A6.e) (0.0008 mol), N-methyl-2-propanamine (0.001 mol), EDCI (0.0012 mol) and HOBT (0.0012 mol) in CH$_2$Cl$_2$ (5 ml) and THF (5 ml) was stirred at room temperature for 12 hours, poured out into H$_2$O and CH$_2$Cl$_2$, then stirred for 5 minutes. The organic layer was separated, dried (MgSO$_4$), filtered and the solvent was evaporated. The residue (0.42 g) was purified by column chromatography over kromasil (eluent: CH$_2$Cl$_2$/CH$_3$OH 99/1; 5 μm). Two fractions were collected and the solvent was evaporated. Yield: 0.14 g of fraction 1 and 0.064 g of fraction 2. Fraction 1 was crystallized from DIPE/diethyl ether. The precipitate was filtered off and dried. Yield: 0.138 g of final compound 41 (31%) (melting point: 126° C.).

e) Preparation of Compound 45

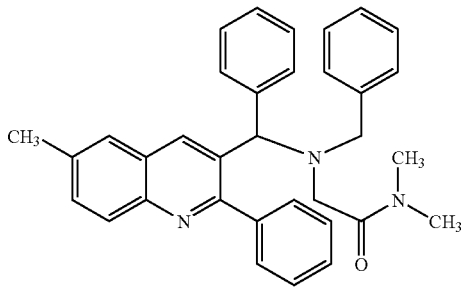

A mixture of intermediate 17 (prepared according to A6.e) (0.0002 mol), dimethylamine (0.0003 mol), Et$_3$N (0.0004 mol), EDCI (0.0003 mol) and HOBT (0.0003 mol) in CH$_2$Cl$_2$ (2 ml) and THF (2 ml) was stirred at room temperature for 12 hours, poured out into H$_2$O and extracted with CH$_2$Cl$_2$. The organic layer was separated, dried (MgSO$_4$), filtered and the solvent was evaporated. The residue (0.1 g) was purified by column chromatography over kromasil (eluent: CH$_2$Cl$_2$/CH$_3$OH 99/1; 10 μm). Two fractions were collected and the solvent was evaporated. Yield: 0.056 g of fraction A and 0.1 g of fraction B. Fraction A was taken up in diethyl ether. The mixture was evaporated. Yield: 0.055 g of final compound 45 (52%).

f) Preparation of Compound 36

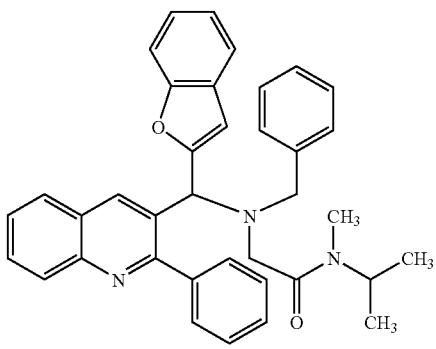

A mixture of intermediate 37 (prepared according to A6.g) (0.0004 mol), N-methyl-2-propanamine (0.0004 mol), EDCI (0.0006 mol) and HOBT (0.0006 mol) in CH$_2$Cl$_2$ (5 ml) and THF (5 ml) was stirred at room temperature for 3 hours. H$_2$O was added. The mixture was extracted with CH$_2$Cl$_2$, then filtered. The organic layer was separated, dried (MgSO$_4$), filtered and the solvent was evaporated. The residue (0.12 g) was purified by column chromatography over kromasil (eluent gradient: CH$_2$Cl$_2$/CH$_3$OH 100/0 to 98/2; 5 μm). The pure fractions were collected and the solvent was evaporated Yield: 0.073 g of final compound 36 (33%).

Example B4 a) Preparation of Compound 104

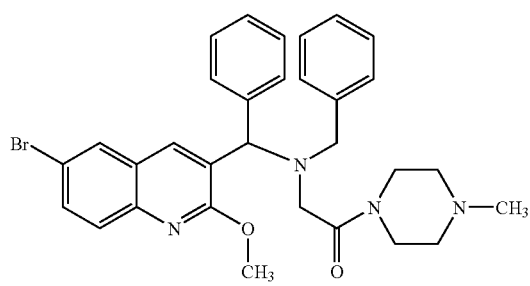

A mixture of intermediate 16 (prepared according to A6.d) (0.0006 mol), 1-methylpiperazine (0.0009 mol), EDCI (0.0009 mol) and HOBT (0.0009 mol) in $CH_2Cl_2$ (8 ml) and THF (8 ml) was stirred at room temperature for 1 hour, then poured out into $H_2O$ and extracted with $CH_2Cl_2$. The organic layer was separated, dried ($MgSO_4$), filtered, and the solvent was evaporated. The residue (0.4 g) was purified by column chromatography over kromasil (eluent: $CH_2Cl_2/CH_3OH$ 95/5; 5 μm). The pure fractions were collected and the solvent was evaporated. The residue was crystallized from DIPE/diethyl ether. The precipitate was filtered off and dried. Yield: 0.107 g of final compound 104 (31%) (melting point: 152° C.).

b) Preparation of Compound 69

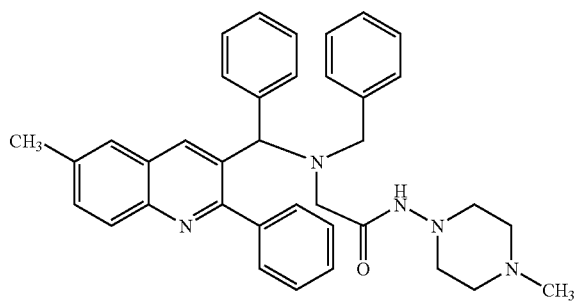

A mixture of intermediate 17 (prepared according to A6.e) (0.0002 mol), 4-methylpiperazineamine (0.0002 mol), EDCI (0.0003 mol) and HOBT (0.0003 mol) in $CH_2Cl_2$ (3 ml) and THF (3 ml) was stirred at room temperature for 12 hours, then evaporated till dryness. The residue was taken up in EtOH. The precipitate was filtered off and dried Yield 0.3 g. This fraction was purified by column chromatography over kromasil (eluent: $CH_2Cl_2/CH_3OH/NH_4OH$ 95/5/0.1; 10 μm). Two fractions were collected and the solvent was evaporated. Yield: 0.082 g of fraction A (34%) and 0.03 g of fraction B. Fraction A was purified by column chromatography over kromasil (eluent: $CH_2Cl_2/CH_3OH/NH_4OH$ 98/2/0.2; 3.5 μm). The pure fractions were collected and the solvent was evaporated. Yield: 0.05 g of final compound 69 (21%).

c) Preparation of Compound 72

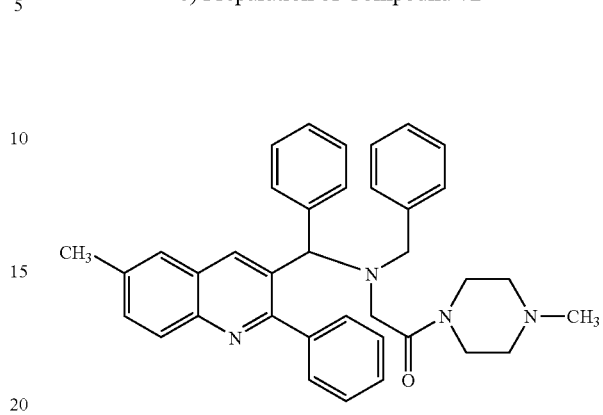

A mixture of intermediate 17 (prepared according to A6.e) (0.0021 mol), N-methylpiperazine (0.0003 mol), EDCI (0.0033 mol) and HOBT (0.0033 mol) in $CH_2Cl_2$ (2 ml) and THF (2 ml) was stirred at room temperature for 12 hours, poured out into $H_2O$ and extracted with $CH_2Cl_2$. The organic layer was separated, dried ($MgSO_4$), filtered, and the solvent was evaporated. The residue (0.1 g) was purified by column chromatography over kromasil (eluent: $CH_2Cl_2/CH_3OH/NH_4OH$ 96/4/0.1; 10 μm). Two fractions were collected and the solvent was evaporated. Yield: 0.06 g of fraction A and 0.007 g of fraction B. Fraction A was dissolved in diethyl ether. The mixture was evaporated. Yield: 0.056 g of final compound 72 (48.5%).

d) Preparation of Compound 66

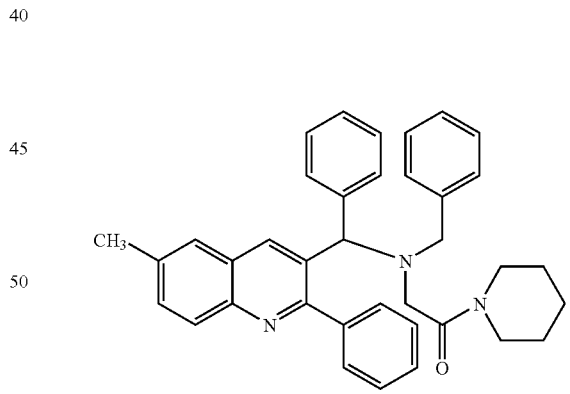

A mixture of intermediate 17 (prepared according to A6.e) (0.0008 mol), piperidine (0.001 mol), EDCI (0.0012 mol) and HOBT (0.0012 mol) in $CH_2Cl_2$ (5 ml) and THF (5 ml) was stirred at room temperature for 12 hours, poured out into $H_2O$ and extracted with $CH_2Cl_2$. The organic layer was separated, dried ($MgSO_4$), filtered and the solvent was evaporated. The residue (0.46 g) was purified by column chromatography over kromasil (eluent: $CH_2Cl_2/CH_3OH$ 99/1; 5 μm). Two fractions were collected and the solvent was evaporated. Yield: 0.094 g of fraction A and 0.048 g of fraction B. Fraction A was crystallized from DIPE/diethyl ether. The precipitate was filtered off and dried. Yield: 0.094 g of final compound 66 (21%) (melting point: 78° C.).

e) Preparation of Compound 114

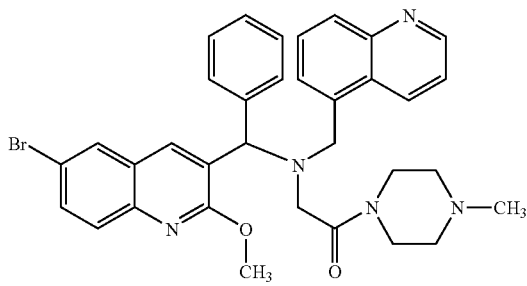

A mixture of intermediate 15 (prepared according to A6.c) (0.0001 mol), N-methyl-piperazine (0.0002 mol), EDCI (0.0002 mol) and HOBT (0.0002 mol) in CH$_2$Cl$_2$ (3 ml) and THF (3 ml) was stirred at room temperature for 12 hours, then poured out into H$_2$O/CH$_2$Cl$_2$. The organic layer was separated, dried (MgSO$_4$), filtered, and the solvent was evaporated. The residue (0.11 g) was purified by column chromatography over kromasil (eluent: CH$_2$Cl$_2$/CH$_3$OH 95/5; 5 µm). The pure fractions were collected and the solvent was evaporated. The residue was dried with diethyl ether. Yield: 0.062 g of final compound 114 (55%).

f) Preparation of Compound 122

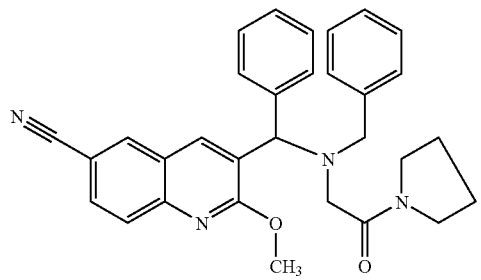

A mixture of intermediate 18 (prepared according to A6.f) (0.0004 mol), pyrrolidine (0.0006 mol), EDCI (0.0006 mol) and HOBT (0.0006 mol) in CH$_2$Cl$_2$ (4 ml) and THF (4 ml) was stirred at room temperature for 18 hours. H$_2$O and CH$_2$Cl$_2$ were added. The mixture was filtered. The filtrate was evaporated. The residue was purified by column chromatography over kromasil (eluent: CH$_2$Cl$_2$/CH$_3$OH 95/5; 10 µm). The pure fractions were collected and the solvent was evaporated. The residue (0.14 g) was crystallized from diethyl ether.

The precipitate was filtered off and dried at 50° C. under vacuo. Yield: 0.068 g of final compound 122 (32%) (melting point: 161° C.).

g) Preparation of Compound 70

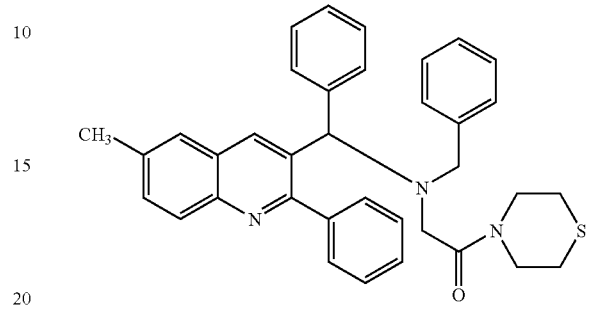

A mixture of intermediate 17 (prepared according to A6.e) (0.0008 mol), thiomorpholine (0.001 mol), EDCI (0.0012 mol) and HOBT (0.0012 mol) in CH$_2$Cl$_2$ (5 ml) and THF (5 ml) was stirred at room temperature for 12 hours, poured out into H$_2$O and CH$_2$Cl$_2$, then stirred for 5 minutes. The organic layer was separated, dried (MgSO$_4$), filtered and the solvent was evaporated. The residue (0.48 g) was purified by column chromatography over kromasil (eluent: CH$_2$Cl$_2$/CH$_3$OH 99/1; 5 µm). The pure fractions were collected and the solvent was evaporated. The residue (0.117 g) was crystallized from DIPE/diethyl ether. The precipitate was filtered off and dried. Yield: 0.029 g of final compound 70 (25%) (melting point: 144° C.).

Example B5

Preparation of Compound 59

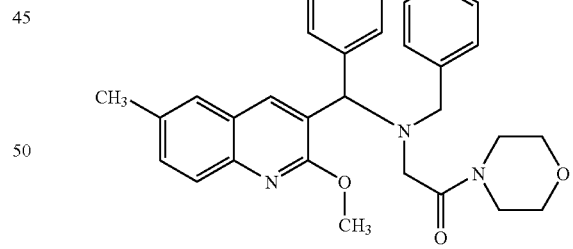

A mixture of final compound 105 (prepared in an analogous manner to B4.a) (0.0002 mol), methylboronic acid (0.0005 mol), Pd(PPh$_3$)$_4$ (0.00002 mol) and Na$_2$CO$_3$ 2M (0.0011 mol) in DME (2.9 ml) was stirred at 90° C. for 6 hours, then cooled to room temperature. H$_2$O was added. The mixture was extracted with CH$_2$Cl$_2$. The organic layer was separated, dried (MgSO$_4$), filtered, and the solvent was evaporated, yielding 0.238 g. This fraction was purified by column chromatography over silica gel (eluent: CH$_2$Cl$_2$/CH$_3$OH 99/1; 10 µm). Two fractions were collected and the solvent was evaporated. Yield: 0.08 g of fraction A and 0.06 g of fraction B. Fraction B was crystallized from DIPE. The precipitate was filtered off and dried. Yield: 0.047 g of final compound 59 (33%) (melting point: 126° C.).

Example B6

Preparation of Compound 154

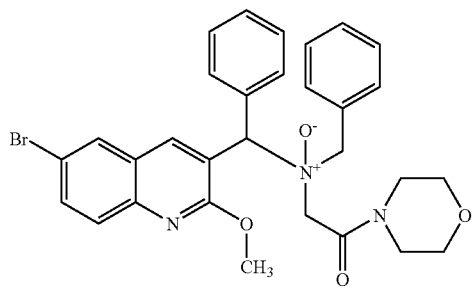

3-Chlorobenzenecarboperoxoic acid (0.0005 mol) was added at 5° C. to a solution of final compound 105 (prepared in an analogous manner to B4.a) (0.0005 mol) in CH$_2$Cl$_2$ (7 ml). The mixture was stirred at room temperature for 24 hours, poured out into H$_2$O and extracted with CH$_2$Cl$_2$. The organic layer was washed with H$_2$O, dried (MgSO$_4$), filtered, and the solvent was evaporated. The residue (0.3 g) was purified by column chromatography over kromasil (eluent: CH$_2$Cl$_2$/CH$_3$OH 100/0 to 98/2; 5 μm). Two fractions were collected and the solvent was evaporated. Yield: 0.07 g of fraction A and 0.013 g of final compound 154 (4%).

Example B7

Preparation of Compound 29

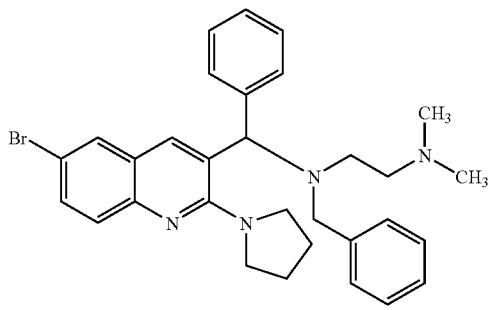

A mixture of intermediate 8 (prepared according to A3.a) (0.0002 mol) in pyrrolidine (0.5 ml) was stirred at 140° C. for 12 hours. The residue was purified by column chromatography over kromasil (eluent: CH$_2$Cl$_2$/CH$_3$OH/NH$_4$OH 98/2/0.1; 10 μm). The pure fractions were collected and the solvent was evaporated. The residue was taken up in diethyl ether and dried. Yield: 0.08 g of final compound 29 (58%).

Example B8 a) Preparation of Compound 51

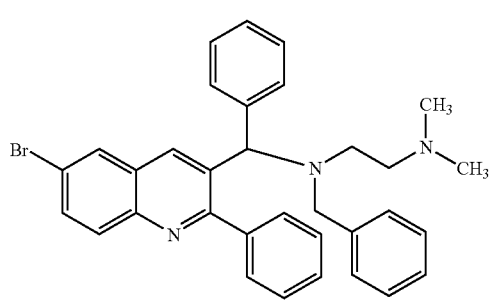

A mixture of intermediate 3 (prepared according to A1.c) (0.0006 mol), N,N-dimethyl-N'-(phenylmethyl)-1,2-ethanediamine (0.0009 mol) and K$_2$CO$_3$ (0.0009 mol) in CH$_3$CN (6 ml) was stirred at 80° C. overnight, poured out into H$_2$O and extracted with EtOAc. The organic layer was separated, dried (MgSO$_4$), filtered, and the solvent was evaporated. The residue (0.44 g) was purified by column chromatography over silica gel (eluent: CH$_2$Cl$_2$/CH$_3$OH/NH$_4$OH 98/2/0.5; 20 μm). The pure fractions were collected and the solvent was evaporated. Yield: 0.17 g of final compound 51 (47%).

b) Preparation of Compound 18

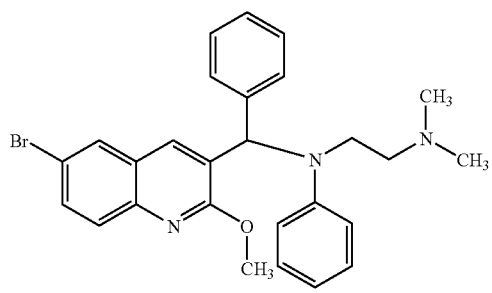

A mixture of intermediate 7 (prepared according to A2.d) (0.0012 mol), N,N-dimethyl-N'-phenyl-1,2-ethanediamine (0.0018 mol) and K$_2$CO$_3$ (0.0018 mol) in CH$_3$CN (10 ml) was stirred at 80° C. overnight, poured out on ice and extracted with CH$_2$Cl$_2$. The organic layer was separated, dried (MgSO$_4$), filtered and the solvent was evaporated. The residue (0.86 g) was purified by column chromatography over kromasil (eluent: CH$_2$Cl$_2$/CH$_3$OH/NH$_4$OH 97/3/0.1; 15-40 μm). Two fractions were collected and the solvent was evaporated. Yield: 0.64 g of fraction A and 0.01 g of fraction B.

Fraction A was crystallized from DIPE. The precipitate was filtered off and dried. Yield: 0.03 g of final compound 18 (melting point: 120° C.).

Example B9

Preparation of Compound 22

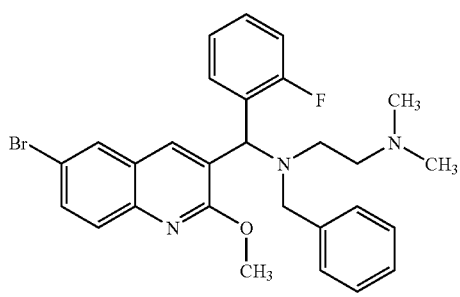

DIAD (0.0027 mol) was added dropwise at 0° C. to a mixture of intermediate 34 (prepared according to A4.b) (0.0014 mol), N,N-dimethyl-N'-(phenylmethyl)-1,2-ethanediamine (0.0027 mol) and PPh$_3$ (0.0027 mol) in THF (15 ml) under N$_2$ flow. The mixture was stirred at room temperature overnight, poured out into H$_2$O and extracted with CH$_2$Cl$_2$. The organic layer was separated, dried (MgSO$_4$), filtered, and the solvent was evaporated. The residue (2.6 g) was purified by column chromatography over silica gel (eluent: CH$_2$Cl$_2$/CH$_3$OH/NH$_4$OH 97/3/0.1; 15-40 μm). The pure fractions were collected and the solvent was evaporated. The residue (0.086 g) was purified by column chromatography over kromasil (eluent: CH$_2$Cl$_2$/CH$_3$OH/NH$_4$OH 98/2/0.1; 10 μm). The pure fractions were collected and the solvent was evaporated. Yield: 0.05 g of final compound 22 (7%).

Example B10 a) Preparation of Compound 20

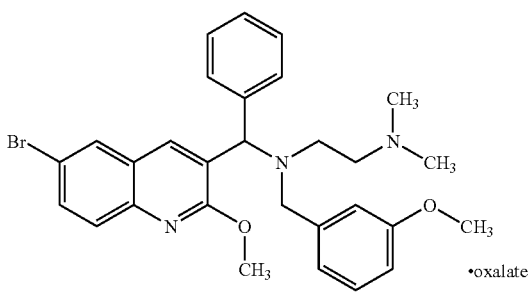

A mixture of intermediate 7 (prepared according to A2.d) (0.0013 mol) and N,N-dimethyl-N'-(2-methoxyphenyl)-1,2-ethanediamine (0.0026 mol) was stirred at 90° C. for 2 hours, then taken up in H$_2$O and CH$_2$Cl$_2$. The organic layer was separated, dried (MgSO$_4$), filtered, and the solvent was evaporated. The residue (0.5 g) was purified by column chromatography over kromasil (eluent: CH$_2$Cl$_2$/CH$_3$OH/NH$_4$OH 95/5/0.1; 10 μm). The pure fractions were collected and the solvent was evaporated. The residue (0.084 g) was dissolved in CH$_3$COCH$_3$ and converted into the ethanedioic acid salt. The precipitate was filtered off and dried. Yield: 0.099 g of final compound 20 (18%) (melting point: 142° C.).

b) Preparation of Compound 37

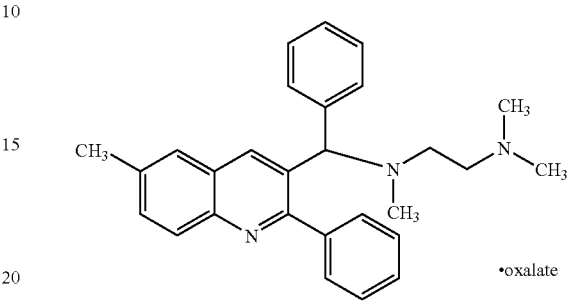

A mixture of intermediate 12 (prepared according to A5.c) (0.0013 mol) and N,N,N'-trimethyl-1,2-ethanediamine (0.0026 mol) was stirred at 90° C. for 2 hours, then taken up in H$_2$O and CH$_2$Cl$_2$. The organic layer was separated, dried (MgSO$_4$), filtered, and the solvent was evaporated. The residue (0.5 g) was purified by column chromatography over kromasil (eluent: CH$_2$Cl$_2$/CH$_3$OH/NH$_4$OH 95/5/0.1; 100 m). The pure fractions were collected and the solvent was evaporated. The residue (0.084 g) was dissolved in CH$_3$COCH$_3$ and converted into the ethanedioic acid salt. The precipitate was filtered off and dried. Yield: 0.099 g of final compound 37 (18%) (melting point: 142° C.).

Example B11 a) Preparation of Compound 83

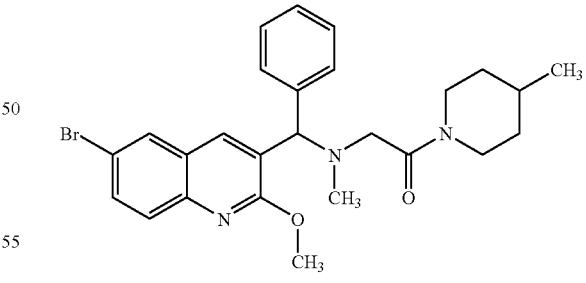

A mixture of intermediate 14 (prepared according to A6.b) (0.17 mmol), 4-methylpiperidine (0.255 mmol), 1-hydroxybenzotriazole (0.255 mmol) and 1-(3-dimethylaminopropyl)-3-ethylcarbodiimide hydrochloride (0.03 g, 0.255 mmol) in THF/CH$_2$Cl$_2$ (1:1, 4 ml) was stirred at room temperature for 12 hours. The mixture was poured into water and the organic layer was separated. The product was purified by chromatography over silica gel (Kromasil 5 μm, 250×20 mm, CH$_2$C$_2$:

100 to CH$_2$Cl$_2$/MeOH; 90:10). The pure fractions were collected and the solvent was evaporated. Yield: final compound 83 (58%).

b) Preparation of Compound 47

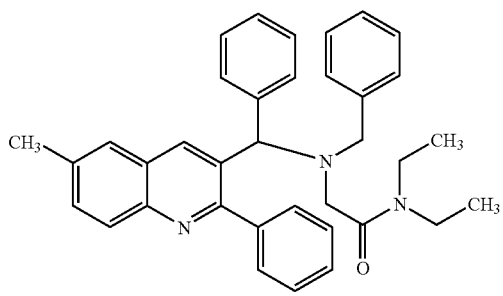

A mixture of intermediate 17 (prepared according to A6.e) (0.15 mmol), diethylamine (0.225 mmol), 1-hydroxybenzotriazole (0.225 mmol) and 1-(3-dimethylaminopropyl)-3-ethylcarbodiimide hydrochloride (0.255 mmol) in THF/CH$_2$Cl$_2$ (1:1, 4 ml) was stirred at room temperature for 12 hours. The mixture was poured into water and the organic layer was separated. The product was purified by chromatography over silica gel (Kromasil 5 μm, 250×20 mm, CH$_2$C$_2$: 100 to CH$_2$Cl$_2$/MeOH: 95:5). The pure fractions were collected and the solvent was evaporated. Yield: final compound 47 (44%).

c) Preparation of Compound 2

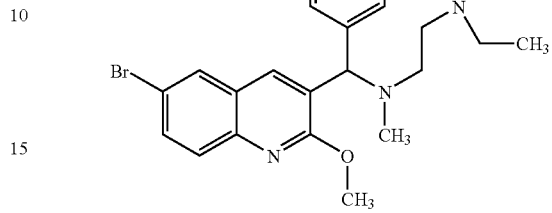

A mixture of intermediate 7 (prepared according to A2.d) (0.25 mmol), N,N-diethyl-N'-methylethylenediamine (0.25 mmol) and potassium carbonate (0.25 mmol) in acetonitrile (5 ml) was stirred at 80° C. for 18 hours. The mixture was poured into water and the organic layer was separated. The product was purified by chromatography over silica gel (Kromasil 5 μm, 250×20 mm, CH$_2$C$_2$: 100 to CH$_2$Cl$_2$/MeOH: 95:5). The pure fractions were collected and the solvent was evaporated. Yield: final compound 2 (69

Tables 1-6 list the compounds that were prepared in an analogous manner as one of the above Examples (Ex. No.).

TABLE 1

| Co. no. | Exp. no. | R¹ | R² | R³ | R⁷ | q | X | R⁴ | R⁵ | R⁶ | Phys. data: melting point (°C.) |
|---|---|---|---|---|---|---|---|---|---|---|---|
| 1 | B11 | —Br | —OCH$_3$ | —CH$_3$ | —H | 1 | —CH$_2$— | —CH$_3$ | —CH$_3$ | phenyl | |
| 2 | B11.c | —Br | —OCH$_3$ | —CH$_3$ | —H | 1 | —CH$_2$— | —CH$_2$CH$_3$ | —CH$_2$CH$_3$ | phenyl | |
| 3 | B3.c | —Br | —OCH$_3$ | —CH$_3$ | —H | 1 | —C(=O)— | —H | —CH$_3$ | phenyl | 190° C. |
| 4 | B3 | —Br | —OCH$_3$ | —CH$_3$ | —H | 1 | —C(=O)— | —CH$_3$ | —CH$_3$ | phenyl | |
| 5 | B3 | —Br | —OCH$_3$ | —CH$_3$ | —H | 1 | —C(=O)— | —CH$_3$ | —CH(CH$_3$)$_2$ | phenyl | |

TABLE 1-continued

| Co. no. | Exp. no. | R¹ | R² | R³ | R⁷ | q | X | R⁴ | R⁵ | R⁶ | Phys. data: melting point (° C.) |
|---|---|---|---|---|---|---|---|---|---|---|---|
| 6 | B3 | —Br | —OCH₃ | —CH₃ | —H | 1 | C=O | —CH₃ | —CH₂CH₂CH₂CH₃ | phenyl | |
| 7 | B3 | —Br | —OCH₃ | —CH₃ | —H | 1 | C=O | —CH₃ | —CH₂CN | phenyl | |
| 8 | B3 | —Br | —OCH₃ | —CH₃ | —H | 1 | C=O | —CH₃ | —CH₂CH₂CH₂N(CH₃)₂ | phenyl | |
| 9 | B3 | —Br | —OCH₃ | —CH₃ | —H | 1 | C=O | —CH₃ | —CH₂CH₂CH₂CH₂N(CH₃)₂ | phenyl | |
| 10 | B3 | —Br | —OCH₃ | —CH₃ | —H | 1 | C=O | —CH₃ | 2-methylphenyl | phenyl | |
| 11 | B3 | —Br | —OCH₃ | | —H | 1 | C=O | —CH₂CH₃ | —CH₂CH₃ | phenyl | |

TABLE 1-continued

| Co. no. | Exp. no. | R¹ | R² | R³ | R⁷ | q | X | R⁴ | R⁵ | R⁶ | Phys. data: melting point (°C.) |
|---|---|---|---|---|---|---|---|---|---|---|---|
| 12 | B3 | —Br | —OCH$_3$ | —CH$_3$ | —H | 1 | C=O | —CH$_2$CH$_3$ | 4-pyridylmethyl | phenyl | |
| 13 | B3 | —Br | —OCH$_3$ | —CH$_3$ | —H | 1 | C=O | —CH$_2$CH$_2$OCH$_3$ | —CH$_2$CH$_2$OCH$_3$ | phenyl | |
| 14 | B3 | —Br | —OCH$_3$ | —CH$_3$ | —H | 1 | C=O | 3-pyridylmethyl | —CH$_2$CH$_2$CN | phenyl | |
| 15 | B3 | —Br | —OCH$_3$ | —CH$_3$ | —Cl | 1 | C=O | —CH$_3$ | —CH$_3$ | phenyl | |
| 16 | B3 | —Br | —OCH$_3$ | —CH(CH$_3$)$_2$ | —H | 1 | —CH$_2$— | —CH$_3$ | —CH$_3$ | phenyl | 130° C. |

TABLE 1-continued
| Co. no. | Exp. no. | R¹ | R² | R³ | R⁷ | q | X | R⁴ | R⁵ | R⁶ | Phys. data: melting point (°C.) |
|---|---|---|---|---|---|---|---|---|---|---|---|
| 17 | B11 | —Br | —OCH₃ |  | —H | 1 | —CH₂— | —CH₃ | —CH₃ | 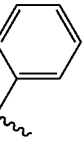 | |
| 18 | B8.b | —Br | —OCH₃ |  | —H | 1 | —CH₂— | —CH₃ | —CH₃ |  | 120° C. |
| 19 | B3 | —Br | —OCH₃ | 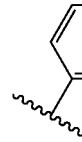 | —H | 1 | 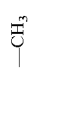 | —CH₃ | —CH₃ | 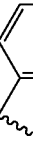 | 192° C. |
| 20 | B10.a | —Br | —OCH₃ | 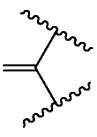 | —H | 1 | —CH₂— | —CH₃ | —CH₃ | 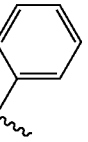 | .oxalate; 148° C. |
| 21 | B3 | —Br | —OCH₃ |  | —H | 1 | —CH₂— | —CH₃ | —CH₃ | 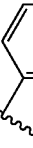 | |

TABLE 1-continued
| Co. no. | Exp. no. | R¹ | R² | R³ | R⁷ | q | X | R⁴ | R⁵ | R⁶ | Phys. data: melting point (° C.) |
|---|---|---|---|---|---|---|---|---|---|---|---|
| 22 | B9 | —Br | —OCH₃ | 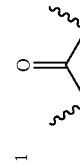 | —H | 1 | —CH₂— | —CH₃ | —CH₃ | 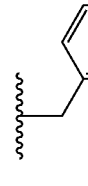 | |
| 23 | B3 | —Br | —OCH₃ | 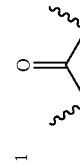 | —H | 1 | 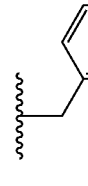 | —H | —CH₃ |  | 172° C. |
| 24 | B3 | —Br | —OCH₃ | 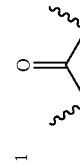 | —H | 1 | 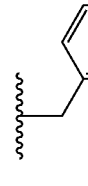 | —CH₃ | —CH₃ |  | 66° C. |
| 25 | B3 | —Br | —OCH₃ | 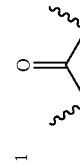 | —H | 1 | 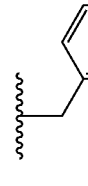 | —CH₃ | —CH₃ |  | |
| 26 | B3 | —Br | —OCH₃ | 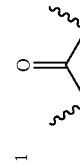 | —H | 1 | 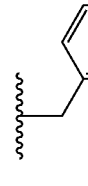 | —CH₃ | —CH₃ |  | 86° C. |

TABLE 1-continued
| Co. no. | Exp. no. | R¹ | R² | R³ | R⁷ | q | X | R⁴ | R⁵ | R⁶ | Phys. data: melting point (°C.) |
|---|---|---|---|---|---|---|---|---|---|---|---|
| 27 | B3 | —Br | —OCH₃ | —CH₃ | —H | 2 | —CH₂— | —CH₃ | —CH₃ | 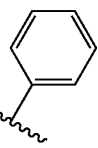 | |
| 28 | B3 | —Br | —OCH₃ | 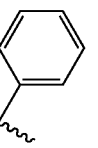 | —H | 2 | —CH₂— | —CH₃ | —CH₃ | 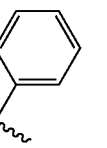 | |
| 29 | B7 | —Br | 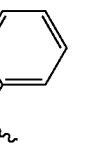 | 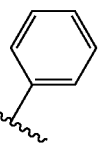 | —H | 1 | —CH₃— | —CH₃ | —CH₃ | | |
| 30 | B3.b | —Br | | | —H | 1 | | —CH₃ | —CH(CH₃)₂ | | |
| 31 | B11 | —CN | —OCH₃ | | —H | 1 | | —CH₃ | —CH₃ | | 191° C. |

TABLE 2

| Co. no. | Exp. no. | R¹ | R³ | q | X | R⁴ | R⁵ | R⁶ | Phys. data: melting point (° C.) |
|---|---|---|---|---|---|---|---|---|---|
| 32 | B4 | —H | benzyl | 1 | C=O | —CH₃ | —CH₃ | phenyl | 86° C. |
| 33 | B4 | —H | benzyl | 1 | C=O | —CH₃ | —CH(CH₃)₂ | phenyl | |
| 34 | B3 | —H | benzyl | 1 | C=O | —CH₃ | —CH(CH₃)₂ | 3-pyridyl | |
| 35 | B3 | —H | benzyl | 1 | C=O | —CH₃ | —CH₃ | 2-benzofuranyl | |
| 36 | B3.f | —H | benzyl | 1 | C=O | —CH₃ | —CH(CH₃)₂ | 2-benzofuranyl | |
| 37 | B10.b | —CH₃ | —CH₃ | 1 | —CH₂— | —CH₃ | —CH₃ | phenyl | .oxalate; 142° C. |
| 38 | B10 | —CH₃ | —CH₃ | 1 | C=O | —H | —CH₃ | phenyl | |
| 39 | B10 | —CH₃ | —CH₃ | 1 | C=O | —CH₃ | —CH₃ | phenyl | |

TABLE 2-continued

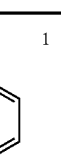

| Co. no. | Exp. no. | R¹ | R³ | q | X | R⁴ | R⁵ | R⁶ | Phys. data: melting point (° C.) |
|---|---|---|---|---|---|---|---|---|---|
| 40 | B4 | —CH$_3$ | benzyl | 1 | C=O | —H | —CH$_3$ | phenyl | |
| 41 | B3.d | —CH$_3$ | benzyl | 1 | C=O | —H | —CH(CH$_3$)$_2$ | phenyl | 126° C. |
| 42 | B4 | —CH$_3$ | benzyl | 1 | C=O | —H | —CH$_2$-cyclopropyl | phenyl | |
| 43 | B4 | —CH$_3$ | benzyl | 1 | C=O | —H | cyclohexyl | phenyl | |
| 44 | B4 | —CH$_3$ | benzyl | 1 | C=O | —H | morpholinyl | phenyl | |
| 45 | B3.e | —CH$_3$ | benzyl | 1 | C=O | —CH$_3$ | —CH$_3$ | phenyl | |
| 46 | B3 | —CH$_3$ | benzyl | 1 | C=O | —CH$_3$ | —CH$_2$CN | phenyl | |
| 47 | B11.b | —CH$_3$ | benzyl | 1 | C=O | —CH$_2$CH$_3$ | —CH$_2$CH$_3$ | phenyl | |

TABLE 2-continued
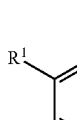
| Co. no. | Exp. no. | R¹ | R³ | q | X | R⁴ | R⁵ | R⁶ | Phys. data: melting point (° C.) |
|---|---|---|---|---|---|---|---|---|---|
| 48 | B11 | —CH₃ | 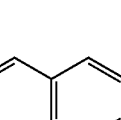 benzyl | 1 | 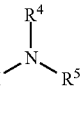 C=O | —CH₂CH₃ |  benzyl | 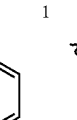 phenyl | |
| 49 | B11 | —CH₃ | 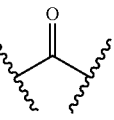 benzyl | 1 | 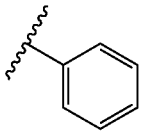 C=O | —CH₂CH₂CH₃ | —CH₂CH₂CH₃ | 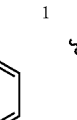 phenyl | |
| 50 | B11 | —CH₃ | 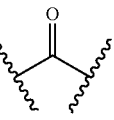 benzyl | 1 | 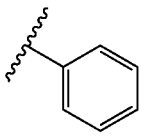 C=O | —CH₂CH₂OCH₃ | —CH₂CH₂OCH₃ | 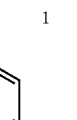 phenyl | |
| 51 | B8.a | —Br | 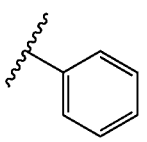 benzyl | 1 | —CH₂— | —CH₃ | —CH₃ | 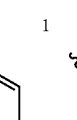 phenyl | |
| 52 | B3 | —Br | 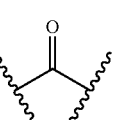 benzyl | 1 | 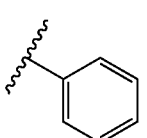 C=O | —H | —CH₃ | 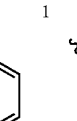 phenyl | |
| 53 | B3.a | —Br | 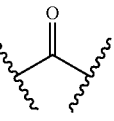 benzyl | 1 | 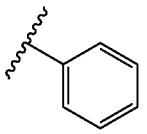 C=O | —CH₃ | —CH₃ | phenyl | 110° C. |

TABLE 3
| Co. no. | Exp. no. | R¹ | R² | R³ | R⁷ | q | 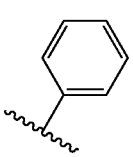 | R⁶ | Phys. data: melting point (° C.) |
|---|---|---|---|---|---|---|---|---|---|
| 54 | B3 | —CH₃ | 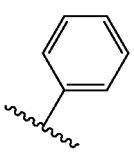 | —CH₃ | —H | 1 |  |  | |
| 55 | B3 | —H |  | 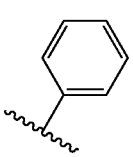 | —H | 1 |  |  | 96° C. |
| 56 | B3 | —H |  |  | —H | 1 |  | 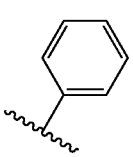 | |
| 57 | B3 | —H |  |  | —H | 1 |  |  | |
| 58 | B3 | —H |  | 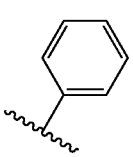 | —H | 1 |  |  | |

TABLE 3-continued

| Co. no. | Exp. no. | R¹ | R² | R³ | R⁷ | q | R⁴–N–R⁵ | R⁶ | Phys. data: melting point (° C.) |
|---|---|---|---|---|---|---|---|---|---|
| 59 | B5 | —CH₃ | —OCH₃ | benzyl | —H | 1 | morpholino | phenyl | 126° C. |
| 60 | B3 | —CH₃ | —OCH₃ | benzyl | —H | 2 | morpholino | phenyl | |
| 61 | B4 | —CH₃ | phenyl | —CH₃ | —H | 1 | thiomorpholino | phenyl | |
| 62 | B4 | —CH₃ | phenyl | —CH₃ | —H | 1 | N-methylpiperazino | phenyl | |
| 63 | B4 | —CH₃ | phenyl | —CH₃ | —H | 1 | morpholino | phenyl | |

TABLE 3-continued

| Co. no. | Exp. no. | R¹ | R² | R³ | R⁷ | q | R⁴-N-R⁵ | R⁶ | Phys. data: melting point (° C.) |
|---|---|---|---|---|---|---|---|---|---|
| 64 | B4 | —CH₃ | phenyl | benzyl | —H | 1 | pyrrolidinyl | phenyl | |
| 65 | B4 | —CH₃ | phenyl | benzyl | —H | 1 | thiazolidinyl | phenyl | |
| 66 | B4.d | —CH₃ | phenyl | benzyl | —H | 1 | piperidinyl | phenyl | |
| 67 | B4 | —CH₃ | phenyl | benzyl | —H | 1 | 4-methylpiperidinyl | phenyl | |
| 68 | B4 | —CH₃ | phenyl | benzyl | —H | 1 | morpholinyl | phenyl | 78° C. |

TABLE 3-continued

| Co. no. | Exp. no. | R$^1$ | R$^2$ | R$^3$ | R$^7$ | q | $\begin{array}{c}R^4\\ \diagdown\\ N-R^5\end{array}$ | R$^6$ | Phys. data: melting point (° C.) |
|---|---|---|---|---|---|---|---|---|---|
| 69 | B4.b | —CH$_3$ | phenyl | benzyl | —H | 1 | 4-methylpiperazin-1-yl | phenyl | |
| 70 | B4.g | —CH$_3$ | phenyl | benzyl | —H | 1 | thiomorpholin-4-yl | phenyl | 144° C. |
| 71 | B4 | —CH$_3$ | phenyl | benzyl | —H | 1 | 2,6-dimethylmorpholin-4-yl | phenyl | |
| 72 | B4.c | —CH$_3$ | phenyl | benzyl | —H | 1 | 4-methylpiperazin-1-yl | phenyl | |

TABLE 3-continued

| Co. no. | Exp. no. | R¹ | R² | R³ | R⁷ | q | R⁴–N–R⁵ | R⁶ | Phys. data: melting point (° C.) |
|---|---|---|---|---|---|---|---|---|---|
| 73 | B4 | —CH₃ | phenyl | benzyl | —H | 1 | isoindolin-2-yl | phenyl | |
| 74 | B4 | —CH₃ | phenyl | benzyl | —H | 1 | 1,2,3,4-tetrahydroisoquinolin-2-yl | phenyl | |
| 75 | B4 | —CH₃ | phenyl | benzyl | —H | 1 | 4-(pyridin-2-yl)piperazin-1-yl | phenyl | |

TABLE 3-continued

| Co. no. | Exp. no. | R¹ | R² | R³ | R⁷ | q | $\begin{matrix}R^4\diagdown N\diagup R^5\\|\end{matrix}$ | R⁶ | Phys. data: melting point (° C.) |
|---|---|---|---|---|---|---|---|---|---|
| 76 | B4 | —CH₃ | phenyl | benzyl | —H | 1 | 4-(pyrimidin-2-yl)piperazin-1-yl | phenyl | |
| 77 | B4 | —CH₃ | phenyl | benzyl | —H | 1 | 4-phenyl-1,2,3,6-tetrahydropyridin-1-yl | phenyl | |
| 78 | B4 | —CH₃ | phenyl | benzyl | —H | 1 | 4-benzylpiperazin-1-yl | phenyl | |
| 79 | B4 | —CH₃ | phenyl | benzyl | —H | 1 | 4-benzylpiperidin-1-yl | phenyl | |

TABLE 3-continued

| Co. no. | Exp. no. | R¹ | R² | R³ | R⁷ | q | NR⁴R⁵ | R⁶ | Phys. data: melting point (°C.) |
|---|---|---|---|---|---|---|---|---|---|
| 80 | B4 | —Br | —OCH₃ | —CH₃ | —H | 1 | pyrrolidinyl | phenyl | 88° C. |
| 81 | B4 | —Br | —OCH₃ | —CH₃ | —H | 1 | thiazolidinyl | phenyl | |
| 82 | B4 | —Br | —OCH₃ | —CH₃ | —H | 1 | piperidinyl | phenyl | |
| 83 | B11.a | —Br | —OCH₃ | —CH₃ | —H | 1 | 4-methylpiperidinyl | phenyl | |
| 84 | B11 | —Br | —OCH₃ | —CH₃ | —H | 1 | 4-methyl-1,4-diazepanyl | phenyl | |

TABLE 3-continued

| Co. no. | Exp. no. | R¹ | R² | R³ | R⁷ | q | $\overset{R^4}{\underset{R^5}{N}}$ | R⁶ | Phys. data: melting point (° C.) |
|---|---|---|---|---|---|---|---|---|---|
| 85 | B11 | —Br | —OCH₃ | —CH₃ | —H | 1 | tetrahydropyridinyl | phenyl | |
| 86 | B11 | —Br | —OCH₃ | —CH₃ | —H | 1 | morpholinyl | phenyl | |
| 87 | B11 | —Br | —OCH₃ | —CH₃ | —H | 1 | 2,6-dimethylmorpholinyl | phenyl | |
| 88 | B11 | —Br | —OCH₃ | —CH₃ | —H | 1 | thiomorpholinyl | phenyl | |
| 89 | B11 | —Br | —OCH₃ | —CH₃ | —H | 1 | 4-methylpiperazinyl | phenyl | 138° C. |

TABLE 3-continued

| Co. no. | Exp. no. | R¹ | R² | R³ | R⁷ | q | (NR⁴R⁵) | R⁶ | Phys. data: melting point (° C.) |
|---|---|---|---|---|---|---|---|---|---|
| 90 | B11 | —Br | —OCH₃ | —CH₃ | —H | 1 | 4-benzylpiperidin-1-yl | phenyl | |
| 91 | B11 | —Br | —OCH₃ | —CH₃ | —H | 1 | 4-benzylpiperazin-1-yl | phenyl | |
| 92 | B11 | —Br | —OCH₃ | —CH₃ | —H | 1 | 4-(pyridin-2-yl)piperazin-1-yl | phenyl | |
| 93 | B11 | —Br | —OCH₃ | —CH₃ | —H | 1 | 4-(pyridin-2-yl)piperazin-1-yl | phenyl | |

TABLE 3-continued
| Co. no. | Exp. no. | R¹ | R² | R³ | R⁷ | q | 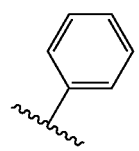 | R⁶ | Phys. data: melting point (° C.) |
|---|---|---|---|---|---|---|---|---|---|
| 94 | B11 | —Br | —OCH₃ | —CH₃ | —H | 1 | 4-phenyl-3,6-dihydro-2H-pyridin-1-yl | phenyl | |
| 95 | B11 | —Br | —OCH₃ | —CH₃ | —H | 1 | isoindolin-2-yl | phenyl | |
| 96 | B11 | —Br | —OCH₃ | —CH₃ | —Cl | 1 | morpholin-4-yl | phenyl | |
| 97 | B11 | —Br | —OCH₃ | —CH₃ | —Cl | 1 | thiomorpholin-4-yl | phenyl | |
| 98 | B11 | —Br | —OCH₃ | —CH(CH₃)₂ | —H | 1 | morpholin-4-yl | phenyl | 68° C. |
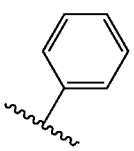

TABLE 3-continued

| Co. no. | Exp. no. | R¹ | R² | R³ | R⁷ | q | R⁴–N–R⁵ | R⁶ | Phys. data: melting point (°C.) |
|---|---|---|---|---|---|---|---|---|---|
| 99 | B11 | —Br | —OCH₃ | phenyl | —H | 1 | morpholinyl | phenyl | 195° C. |
| 100 | B11 | —Br | —OCH₃ | phenyl | —H | 1 | thiomorpholinyl | phenyl | 208° C. |
| 101 | B11 | —Br | —OCH₃ | furan-2-ylmethyl | —H | 1 | morpholinyl | phenyl | — |
| 102 | B11 | —Br | —OCH₃ | furan-3-ylmethyl | —H | 1 | morpholinyl | phenyl | 138° C. |
| 103 | B11 | —Br | —OCH₃ | benzyl | —H | 1 | pyrrolidinyl | phenyl | 142° C. |

TABLE 3-continued

| Co. no. | Exp. no. | R¹ | R² | R³ | R⁷ | q | R⁴–N–R⁵ | R⁶ | Phys. data: melting point (° C.) |
|---|---|---|---|---|---|---|---|---|---|
| 104 | B4.a | —Br | —OCH₃ | benzyl | —H | 1 | 4-methylpiperazin-1-yl | phenyl | 152° C. |
| 105 | B4 | —Br | —OCH₃ | benzyl | —H | 1 | morpholin-4-yl | phenyl | 160° C. |
| 106 | B4 | —Br | —OCH₃ | benzyl | —H | 1 | thiomorpholin-4-yl | phenyl | 168° C. |
| 107 | B4 | —Br | —OCH₃ | benzyl | —H | 1 | 1,3-oxazinan-3-yl | phenyl | 136° C. |
| 108 | B4 | —Br | —OCH₃ | 2-chlorobenzyl | —H | 1 | morpholin-4-yl | phenyl | 90° C. |

TABLE 3-continued

| Co. no. | Exp. no. | R¹ | R² | R³ | R⁷ | q | R⁴-N-R⁵ | R⁶ | Phys. data: melting point (° C.) |
|---|---|---|---|---|---|---|---|---|---|
| 109 | B4 | —Br | —OCH₃ | 3,5-difluorobenzyl | —H | 1 | morpholinyl | phenyl | 198° C. |
| 110 | B4 | —Br | —OCH₃ | (pyridin-2-yl)methyl | —H | 1 | morpholinyl | phenyl | |
| 111 | B4 | —Br | —OCH₃ | (pyridin-3-yl)methyl | —H | 1 | morpholinyl | phenyl | 156° C. |
| 112 | B4 | —Br | —OCH₃ | benzyl | —H | 1 | morpholinyl | phenyl | |
| 113 | B4 | —Br | —OCH₃ | (quinolin-2-yl)methyl | —H | 1 | thiomorpholinyl | phenyl | 126° C. |

TABLE 3-continued

| Co. no. | Exp. no. | R¹ | R² | R³ | R⁷ | q | R⁴ R⁵ (NR⁴R⁵) | R⁶ | Phys. data: melting point (° C.) |
|---|---|---|---|---|---|---|---|---|---|
| 114 | B4.e | —Br | —OCH₃ | quinolin-5-ylmethyl | —H | 1 | 4-methylpiperazin-1-yl | phenyl | |
| 115 | B4 | —Br | —OCH₃ | quinolin-5-ylmethyl | —H | 1 | thiomorpholin-4-yl | phenyl | |
| 116 | B4 | —Br | —OCH₃ | quinolin-5-ylmethyl | —H | 1 | morpholin-4-yl | phenyl | |
| 117 | B4 | —Br | —OCH₃ | isoquinolin-5-ylmethyl | —H | 1 | thiomorpholin-4-yl | phenyl | |

TABLE 3-continued
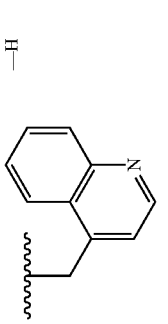
| Co. no. | Exp. no. | R¹ | R² | R³ | R⁷ | q | 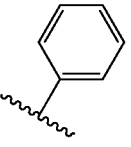 | R⁶ | Phys. data: melting point (° C.) |
|---|---|---|---|---|---|---|---|---|---|
| 118 | B4 | —Br | —OCH₃ | 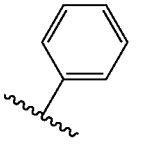 | —H | 1 | 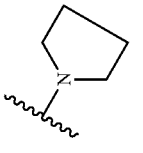 | 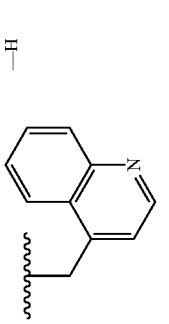 | |
| 119 | B4 | —Br | —OCH₃ | 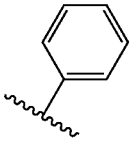 | —H | 1 | 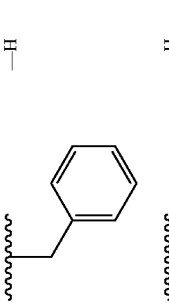 | 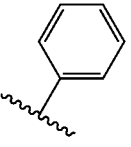 | |
| 120 | B4 | —Br | —OCH₃ | 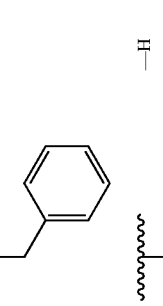 | —H | 2 | 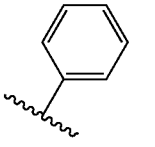 | 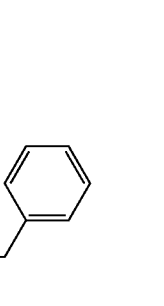 | |
| 121 | B4 | —Br | 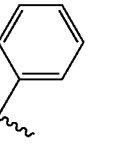 |  | —H | 1 |  |  | |
| 122 | B4.f | —CN | —OCH₃ |  | —H | 1 | | | 161° C. |

TABLE 3-continued

| Co. no. | Exp. no. | R¹ | R² | R³ | R⁷ | q | R⁴—N—R⁵ | R⁶ | Phys. data: melting point (° C.) |
|---|---|---|---|---|---|---|---|---|---|
| 123 | B4 | —CN | —OCH₃ | benzyl | —H | 1 | N-methylpiperazinyl | phenyl | 158° C. |
| 124 | B4 | —CN | —OCH₃ | benzyl | —H | 1 | morpholinyl | phenyl | 140° C. |
| 125 | B4 | —CN | —OCH₃ | benzyl | —H | 1 | thiomorpholinyl | phenyl | 193° C. |
| 126 | B4 | —H | phenyl | benzyl | —H | 1 | piperidinyl | phenyl | |
| 127 | B4 | —H | phenyl | benzyl | —H | 1 | thiomorpholinyl | phenyl | |

TABLE 4

| Co. no. | Exp. no. | R¹ | R² | R³ | q | R⁶ | R⁷ | Phys. data: melting point (° C.) |
|---|---|---|---|---|---|---|---|---|
| 128 | B2 | —H | phenyl | benzyl | 1 | phenyl | —H | |
| 129 | B2.e | —H | phenyl | benzyl | 1 | pyridin-3-yl | —H | |
| 130 | B2.h | —H | phenyl | benzyl | 1 | benzofuran-2-yl | —H | |
| 131 | B2.a | —Br | —OCH₃ | —CH₃ | 1 | phenyl | —H | |
| 132 | B2.g | —Br | —OCH₃ | —CH₃ | 1 | phenyl | —Cl | |
| 133 | B2 | —Br | —OCH₃ | isopropyl | 1 | phenyl | —H | |
| 134 | B2 | —Br | —OCH₃ | isobutyl | 1 | phenyl | —H | |
| 135 | B2 | —Br | —OCH₃ | furan-2-ylmethyl | 1 | phenyl | —H | 98° C. |
| 136 | B2 | —Br | —OCH₃ | furan-3-ylmethyl | 1 | phenyl | —H | 120° C. |

TABLE 4-continued
| Co. no. | Exp. no. | R¹ | R² | R³ | q | R⁶ | R⁷ | Phys. data: melting point (° C.) |
|---|---|---|---|---|---|---|---|---|
| 137 | B2.b | —Br | —OCH₃ | 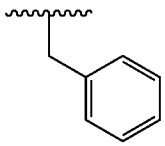 | 1 | 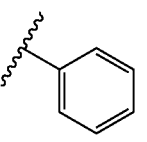 | —H | |
| 138 | B2 | —Br | —OCH₃ | 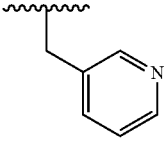 | 1 | 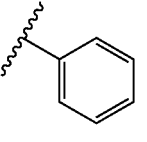 | —H | |
| 139 | B2 | —Br | —OCH₃ | 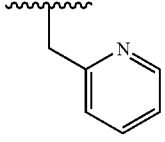 | 1 | 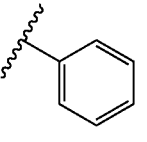 | —H | |
| 140 | B2 | —Br | —OCH₃ | 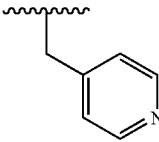 | 1 | 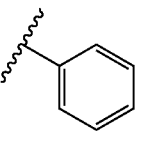 | —H | |
| 141 | B2.k | —Br | —OCH₃ | 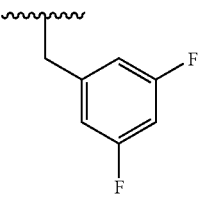 | 1 | 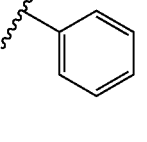 | —H | |
| 142 | B2 | —Br | —OCH₃ | 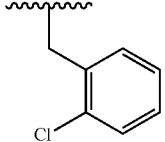 | 1 | 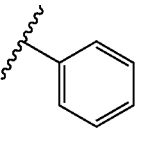 | —H | |
| 143 | B2.i | —Br | —OCH₃ | 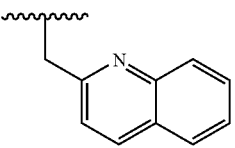 | 1 | 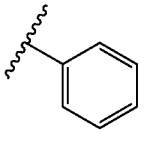 | —H | 220° C. |
| 144 | B2 | —Br | —OCH₃ | 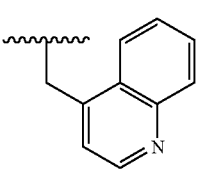 | 1 | 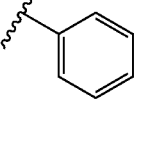 | —H | 128° C. |

TABLE 4-continued
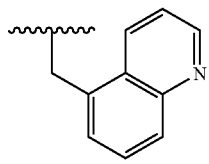
| Co. no. | Exp. no. | R¹ | R² | R³ | q | R⁶ | R⁷ | Phys. data: melting point (° C.) |
|---|---|---|---|---|---|---|---|---|
| 145 | B2.c | —Br | —OCH₃ | 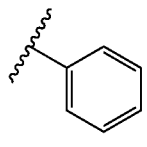 | 1 | 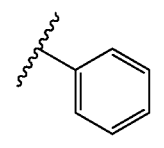 | —H | 96° C. |
| 146 | B1.a | —Br | 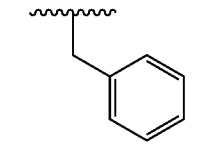 | 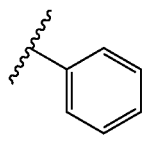 | 1 | 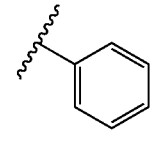 | —H | |
| 147 | B1 | —Br | 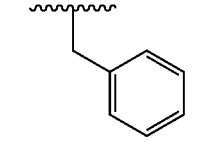 | 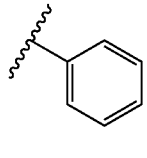 | 2 | 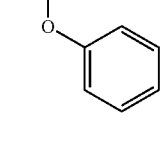 | —H | |
| 148 | B2.j | —Br | 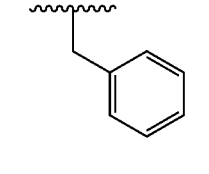 | 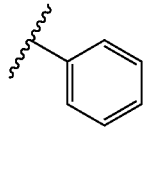 | 1 | 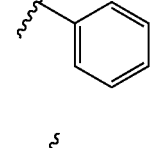 | —H | |
| 149 | B1 | —CH₃ | 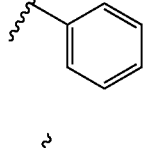 | —CH₃ | 1 | 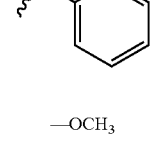 | —H | |
| 150 | B1.b | —CH₃ | 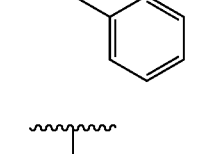 | 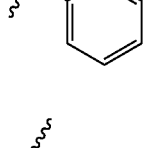 | 1 | 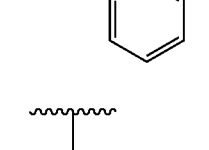 | —H | |
| 151 | B2.d | —CN | —OCH₃ | 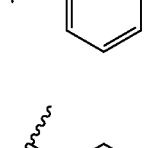 | 1 | 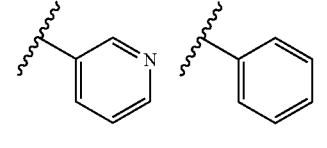 | —H | 148° C. |
| 152 | B1.c | 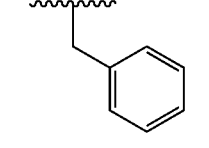 | 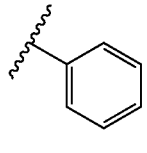 | 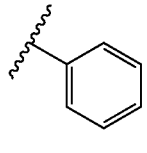 | 1 |  | —H | |

TABLE 5

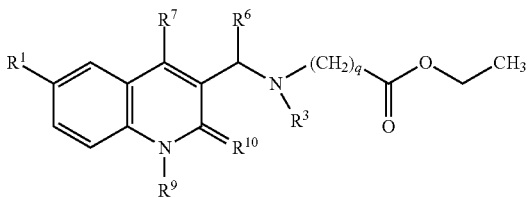

| Co. no. | Exp. no. | $R^1$ | $R^3$ | q | $R^6$ | $R^7$ | $R^9$ | $R^{10}$ | Phys. data: melting point (° C.) |
|---|---|---|---|---|---|---|---|---|---|
| 153 | B2.f | —Br | —CH$_3$ | 1 | 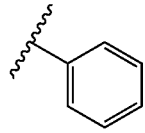 | —H | —CH$_3$ | O | |

TABLE 6

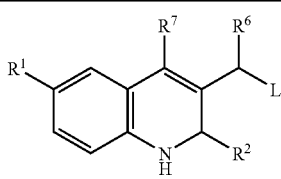

| Co. no. | Exp. no. | $R^1$ | $R^2$ | $R^6$ | $R^7$ | L | Phys. data: melting point (° C.) |
|---|---|---|---|---|---|---|---|
| 154 | B6 | —Br | —OCH$_3$ | ![phenyl] | —H | ![morpholine-N-oxide-benzyl group] | |

C. Analytical Data

For a number of compounds, either melting points or LCMS data were recorded.

1. Melting Points

If possible, melting points (or ranges) were obtained with a Leica VMHB Koffler bank. The melting points are uncorrected.

2. LCMS Conditions

Method 1:

LCMS was carried out (electrospray ionisation in positive mode, scanning mode from 100 to 900 amu) on a Kromasil C18 (Interchim, Montluçon, FR) 5 μm, 4.6×150 mm); Flow rate 1 ml/minute. Two mobile phases (mobile phase A: 30% 6.5 mM ammonium acetate+40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes).

Method 2:

LCMS was carried out (electrospray ionisation in both positive and negative (pulsed)) on a Kromasil C18 (Interchim, Montluçon, FR) 3.5 μm, 4.6×100 mm); Flow rate 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute).

Method 3:

LCMS was carried out (electrospray ionisation in both positive and negative (pulsed) mode scanning from 100 to 1000 amu) on a Sunfire C18 (Waters, Millford USA) 3.5 μm, 4.6×100 mm); Flow rate 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute).

Method 4:

LCMS was carried out (electrospray ionisation in positive mode, scanning mode from 100 to 900 amu) on a Xterra MS C18 (Waters, Milford, Mass.) 5 μm, 3.9×150 mm); Flow rate 1 ml/minute. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 minutes to 100% B in 5 minutes, 100% B for 6 minutes to 100% A in 3 minutes, and reequilibrate with 100% A for 3 minutes).

TABLE 7

LCMS parent peak

| Compound No | LCMS parent peak (MH$^+$) | LCMS method |
|---|---|---|
| 1 | 428 | 1 |
| 2 | 456 | 2 |
| 4 | 442 | 1 |
| 5 | 470 | 1 |
| 6 | 484 | 1 |
| 7 | 467 | 1 |
| 8 | 499 | 1 |
| 9 | 513 | 1 |
| 10 | 518 | 1 |
| 11 | 470 | 1 |
| 12 | 533 | 1 |
| 13 | 530 | 1 |
| 14 | 558 | 1 |
| 16 | 470 | 1 |
| 17 | 484 | 4 |
| 21 | 504 | 1 |
| 22 | 522 | 1 |
| 25 | 569 | 1 |
| 27 | 442 | 2 |
| 28 | 513 | 2 |
| 29 | 543 | 1 |
| 30 | 608 | 1 |
| 33 | 514 | 2 |
| 34 | 515 | 1 |
| 35 | 526 | 1 |
| 36 | 554 | 1 |
| 38 | 410 | 1 |
| 39 | 424 | 1 |
| 40 | 486 | 1 |
| 42 | 526 | 1 |
| 43 | 554 | 1 |
| 44 | 557 | 1 |
| 45 | 500 | 1 |
| 46 | 525 | 1 |
| 47 | 528 | 1 |
| 48 | 590 | 1 |
| 49 | 556 | 1 |
| 50 | 588 | 1 |
| 51 | 550 | 1 |
| 52 | 550 | 4 |
| 54 | 450 | 1 |
| 56 | 545 | 1 |
| 57 | 552 | 1 |
| 58 | 584 | 1 |
| 60 | 510 | 1 |
| 61 | 482 | 1 |
| 62 | 479 | 1 |
| 63 | 466 | 1 |
| 64 | 526 | 1 |
| 65 | 544 | 1 |
| 67 | 554 | 1 |
| 68 | 542 | 1 |
| 69 | 286 | 3 |
| 71 | 570 | 1 |
| 72 | 555 | 1 |
| 73 | 574 | 1 |
| 74 | 588 | 1 |
| 75 | 618 | 1 |
| 76 | 619 | 1 |
| 77 | 614 | 1 |
| 78 | 631 | 1 |
| 79 | 630 | 1 |
| 81 | 486 | 1 |
| 82 | 482 | 1 |
| 83 | 496 | 1 |
| 84 | 511 | 1 |
| 85 | 480 | 1 |
| 86 | 484 | 1 |
| 87 | 512 | 1 |
| 88 | 500 | 1 |

TABLE 7-continued

LCMS parent peak

| Compound No | LCMS parent peak (MH$^+$) | LCMS method |
|---|---|---|
| 90 | 572 | 1 |
| 91 | 573 | 1 |
| 92 | 561 | 1 |
| 93 | 235 | 1 |
| 94 | 556 | 1 |
| 95 | 516 | 1 |
| 97 | 536 | 1 |
| 98 | 512 | 1 |
| 101 | 550 | 1 |
| 111 | 561 | 1 |
| 113 | 627 | 1 |
| 114 | 624 | 1 |
| 115 | 627 | 1 |
| 116 | 611 | 1 |
| 117 | 627 | 1 |
| 118 | 611 | 1 |
| 119 | 334 | 1 |
| 120 | 574 | 1 |
| 121 | 620 | 1 |
| 126 | 526 | 1 |
| 127 | 544 | 1 |
| 128 | 487 | 1 |
| 129 | 488 | 1 |
| 130 | 527 | 1 |
| 131 | 443 | 1 |
| 132 | 477 | 1 |
| 133 | 471 | 1 |
| 134 | 485 | 1 |
| 137 | 519 | 1 |
| 138 | 520 | 1 |
| 139 | 520 | 1 |
| 140 | 520 | 1 |
| 141 | 555 | 1 |
| 142 | 555 | 1 |
| 146 | 565 | 1 |
| 147 | 533 | 1 |
| 148 | 581 | 1 |
| 149 | 425 | 1 |
| 150 | 501 | 1 |
| 152 | 564 | 1 |
| 153 | 443 | 1 |
| 154 | 576 | 1 |

D. Pharmacological Examples

D.1. In-Vitro Method for Testing Compounds Against *M. tuberculosis*.

Flat-bottom, sterile 96-well plastic microtiter plates were filled with 100 µl of Middlebrook (1×) broth medium. Subsequently, stock solutions (10× final test concentration) of compounds were added in 25 µl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 5000 CFU per well of *Mycobacterium tuberculosis* (strain H37RV), in a volume of 100 µl in Middlebrook (1×) broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 μl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods and expressed as $pIC_{50}$ values. The results are shown in Table 8.

D.2. In-Vitro Method for Testing Compounds for Anti-Bacterial Activity Against Strain *M. Smegmatis* ATCC607

Flat-bottom, sterile 96-well plastic microtiter plates were filled with 180 μl of sterile deionized water, supplemented with 0.25% BSA. Subsequently, stock solutions (7.8× final test concentration) of compounds were added in 45 μl volumes to a series of duplicate wells in column 2 so as to allow evaluation of their effects on bacterial growth. Serial five-fold dilutions (45 μl in 180 μl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 μl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 μl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The percentage growth inhibition achieved by the compounds was calculated according to standard methods and expressed as $pIC_{50}$ values. The results are shown in Table 8.

TABLE 8

Results of an in vitro-screening of the compounds according to the invention for *M. smegmatis* ($pIC_{50}$) and *M. tuberculosis* ($pIC_{50}$).

| Co. No. | *M. smegmatis* $pIC_{50}$ | *M. tuberculosis* $pIC_{50}$ |
|---|---|---|
| 21 | 5.8 | 5.1 |
| 1 | 5.1 | — |
| 18 | 5.7 | — |
| 2 | 5.7 | — |
| 27 | 5.5 | — |
| 131 | 6.0 | 4.5 |
| 28 | 5.1 | — |
| 146 | 6.3 | 4.3 |
| 51 | 6 | 5.1 |
| 150 | 6.4 | 4.4 |
| 152 | 5.6 | — |
| 53 | 6.5 | 4.7 |
| 4 | 5.1 | — |
| 86 | 4.9 | — |
| 80 | 5.1 | — |
| 89 | 5 | — |
| 88 | 4.9 | 4.05 |
| 3 | 4.05 | <4 |
| 52 | 5.8 | — |
| 122 | 4.2 | — |
| 123 | 5.2 | — |
| 82 | 4.4 | — |
| 11 | 5.1 | — |
| 5 | 5.1 | — |
| 14 | 5.2 | — |
| 7 | 4.9 | — |
| 8 | 5.1 | — |
| 85 | 5.1 | — |
| 6 | 5.1 | — |
| 124 | 5.05 | — |
| 91 | 4.1 | — |
| 84 | 5.1 | — |
| 13 | 4.6 | — |
| 83 | 5.6 | — |
| 95 | 4.9 | — |
| 10 | 4.7 | — |
| 12 | 5.1 | — |
| 81 | 5 | — |
| 87 | 5.1 | — |
| 92 | 5.1 | — |
| 9 | 5 | — |
| 133 | 5.7 | 4.4 |
| 16 | 4.4 | — |
| 17 | 5.3 | — |
| 15 | 4.8 | — |
| 96 | 5.2 | — |
| 97 | 4.4 | 4.2 |
| 24 | 5.1 | — |
| 105 | 6.0 | — |
| 104 | 5.8 | — |
| 106 | 6.4 | <4 |
| 103 | 4.5 | — |
| 32 | 5.7 | — |
| 55 | 6.0 | 4.3 |
| 98 | 5.3 | — |
| 111 | 5.8 | — |
| 139 | 4.3 | — |
| 107 | 5.8 | — |
| 54 | 5.0 | — |
| 61 | 5.1 | — |
| 62 | 5.1 | — |
| 63 | 5.1 | — |
| 39 | 4.5 | — |
| 38 | 4.5 | — |
| 154 | 5.4 | — |
| 108 | 5.9 | 4.0 |
| 64 | 6.5 | 5.0 |
| 68 | 6.5 | 5.1 |
| 113 | 4.5 | — |
| 115 | 4.8 | — |
| 114 | 4.7 | — |
| 116 | 5.3 | — |
| 25 | 5.4 | — |
| 20 | 5.9 | — |
| 117 | 4.3 | — |
| 118 | 5.6 | — |
| 26 | 5.7 | — |
| 119 | 5.5 | — |
| 101 | 4.9 | — |
| 59 | 5.8 | — |
| 110 | 5.2 | — |
| 145 | 4.5 | — |
| 136 | 4.4 | — |
| 37 | 4.7 | — |
| 120 | 5.6 | — |
| 22 | 5.8 | — |
| 102 | 5.8 | — |
| 60 | 5.3 | — |
| 74 | 5.2 | 5.0 |
| 66 | 5.6 | 4.4 |

TABLE 8-continued

Results of an in vitro-screening of the compounds according to the invention for M. smegmatis (pIC$_{50}$) and M. tuberculosis (pIC$_{50}$).

| Co. No. | M. smegmatis pIC$_{50}$ | M. tuberculosis pIC$_{50}$ |
|---|---|---|
| 41 | 7.0 | 5.2 |
| 46 | 5.8 | 5.0 |
| 75 | 4.0 | 5.4 |
| 49 | 5.2 | 4.6 |
| 77 | 4.0 | — |
| 78 | 4.0 | 6.05 |
| 79 | 4.0 | 5.7 |
| 67 | 6.0 | 5.7 |
| 73 | 4.0 | 4.5 |
| 65 | 6.5 | 5.0 |
| 71 | 5.7 | 5.1 |
| 76 | 4.0 | 5.0 |
| 70 | 6.6 | 5.5 |
| 47 | 6.5 | 5.2 |
| 48 | 4.0 | 4.1 |
| 50 | 5.8 | — |
| 40 | 5.6 | — |
| 72 | 5.8 | — |
| 45 | 6.0 | 5.0 |
| 112 | 5.8 | — |
| 30 | 6.2 | — |
| 33 | 6.5 | — |
| 127 | 6.5 | — |
| 126 | 6.4 | — |
| 42 | 5.8 | — |
| 44 | 5.1 | — |
| 43 | 5.2 | — |
| 34 | 5.8 | — |
| 56 | 5.8 | — |
| 129 | 5.8 | — |
| 36 | 6.5 | — |
| 58 | 6.1 | — |
| 35 | 5.6 | — |
| 57 | 5.9 | — |
| 69 | 5.8 | — |

D.3. In-Vitro Method for Testing Compounds for Anti-Bacterial Activity Against Various Non-Mycobacterial Strains Preparation of Bacterial Suspensions for Susceptibility Testing The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates to detect the TCID$_{50}$, in which the TCID50 represents the dilution that gives rise to bacterial growth in 50% of inoculated cultures.

In general, an inoculum level of approximately 100 TCID$_{50}$ was used for susceptibility testing.

Anti Bacterial Susceptibility Testing: IC$_{90}$ Determination Microtitre Plate Assay Flat-bottom, sterile 96-well plastic microtiter plates were filled with 180 μl of sterile deionized water, supplemented with 0.25% BSA. Subsequently, stock solutions (7.8× final test concentration) of compounds were added in 45 μl volumes in column 2. Serial five-fold dilutions (45 μl in 180 μl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 μl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 μl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The IC$_{90}$ (expressed in μg/ml) was defined as the 90% inhibitory concentration for bacterial growth. The results are shown in Table 9.

Agar Dilution Method.

MIC$_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard—sixth edition Time Kill Assays Bactericidal or bacteriostatic activity of the compounds may be determined in a time kill assay using the broth microdilution method *. In a time kill assay on Staphylococcus aureus and methicillin resistant S. aureus (MRSA), the starting inoculum of S. aurues and MRSA is 10$^6$ CFU/ml in Muller Hinton broth. The antibacterial compounds are used at the concentration of 0.1 to 10 times the MIC (i.e. IC$_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution (10$^{-1}$ to 10$^{-6}$) in sterile PBS and plating (200 μl) on Mueller Hinton agar. The plates are incubated at 37° C. for 24 hrs and the number of colonies are determined. Killing curves can be constructed by plotting the log$_{10}$ CFU per ml versus time. A bactericidal effect is commonly defined as 3-log$_{10}$ decrease in number of CFU per ml as compared to untreated inoculum. The potential carryover effect of the drugs is removed by serial dilutions and counting the colonies at highest dilution used for plating.

Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of S. aureus (ATCC29213) stock in 100 ml Mueller Hinton flasks and incubate in a shaker-incubator for 24 hrs at 37° C. (300 rpm). Measure OD$_{405}$ nm and calculate the CFU/ml. Dilute the cultures to 1×10$^6$ CFU/ml (final concentration for ATP measurement: 1×10$^5$ CFU/100 μl per well) and add test compound at 0.1 to 10 times the MIC (i.e. IC$_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 μl of the same sample. Add 100 μl Luciferase reagent to each well by using the injector system. Measure the luminescence for 1 sec.

TABLE 9

IC90 values (µg/ml) determined according to the Microtitre plate assay.

| Comp. No. | BSU 43639 | ECO 25922 | EFA 14506 | EFA 29212 | LMO 49594 | PAE 27853 | SMU 33402 | SPN 6305 | SPY 8668 | STA 43300 | STA 25923 | STA 29213 | STA RMETH |
|---|---|---|---|---|---|---|---|---|---|---|---|---|---|
| 21 | 10.1 | 12.7 | 10.1 | 12.7 | 12.7 | 12.7 | 10.1 | 12.7 | 10.1 | | 11.3 | 10.1 | |
| 147 | | 13.4 | | | | | | | | | | | |
| 137 | | 13.0 | | | | | | | | | 11.6 | | |
| 146 | | 14.2 | | | | | | | | | | | |
| 51 | | 13.8 | 11.0 | 13.8 | 13.8 | 11.0 | 6.9 | 2.8 | 2.8 | | 12.3 | 11.0 | 12.3 |
| 152 | | 14.2 | | | | | | | | | | | |
| 53 | | 14.2 | | | | | | | | | | | |
| 52 | | 13.8 | | | | | | | | | | | |
| 122 | | 12.3 | | | | | | | | | | | |
| 123 | | 13.1 | | | | | | 13.1 | | | | | |
| 11 | | | | | | | | | | | | 11.8 | |
| 124 | | 12.7 | | | | | | | | | | | |
| 105 | | 14.1 | | | | | | | | | | | |
| 104 | 12.8 | 14.4 | | | 14.4 | 11.4 | 14.4 | 11.4 | | | 12.8 | 11.4 | 12.8 |
| 106 | | 14.5 | | | | | | | | | | | |
| 103 | | 13.7 | | | | | | | | | | | |
| 55 | | 12.9 | | | | | | | | | | | |
| 111 | | 14.1 | | | | | | | | | | | |
| 107 | | 14.4 | | | | | | | | | | | |
| 108 | | 14.9 | | | | | | | | | | | |
| 114 | | 62.5 | | 12.5 | 49.6 | | 15.7 | | | 12.5 | | 12.5 | |
| 20 | | 15.7 | | 15.7 | 15.7 | | 12.5 | 15.7 | 12.5 | | | 14.0 | 14.0 |
| 59 | | 12.4 | | | | | | | | | | | |
| 120 | | 14.4 | | | | | | | | | | | |
| 22 | 41.5 | 52.2 | 41.5 | 10.4 | 8.3 | 13.1 | | | | | 8.3 | 10.4 | |
| 102 | | 13.8 | | | | | | | | | | | |
| 74 | | 14.8 | | | | | | | | | | | |
| 66 | | 13.6 | | | | | | | | | | | |
| 41 | | 13.3 | | | | | | | | | | | |
| 65 | | 13.7 | | | | | | | | | | | |
| 70 | | 14.0 | | 14.0 | 14.0 | | | | | | | | |
| 72 | 8.8 | 55.5 | | | 11.1 | | 13.9 | | | 11.1 | 11.1 | 11.1 | |
| 112 | | | | | | | | | | | | 14.1 | |
| 34 | | | | | | | | | | | | 51.5 | |
| 69 | | | | | | | | | | | | 9.0 | |

The invention claimed is:

1. A compound according to the Formula (Ia)

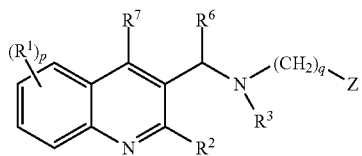

(Ia)

a pharmaceutically acceptable acid or base addition salt thereof, a quaternary amine thereof, a stereochemically isomeric form thereof, a tautomeric form thereof, or a N-oxide form thereof, wherein:

P is an integer equal to zero, 1, 2, 3 or 4;
q is an integer equal to 1, 2 or 3;
Z is a radical selected from formulae:

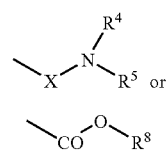

$R^1$ is cyano, halo, alkyl, haloalkyl, hydroxy, alkyloxy, alkylthio, alkyloxyalkyloxy, alkylthioalkyl, arylalkyl, di(aryl)alkyl, aryl or Het;

$R^2$ is hydrogen, alkyloxy, aryl, aryloxy, hydroxy, mercapto, alkyloxyalkyloxy, alkylthio, or mono or di(alkyl)amino, $R^3$ is arylalkyl, aryl, mono- or di-alkylaminoalkyl, Het or Het-alkyl;

$R^4$ and $R^5$ each independently is hydrogen; alkyl; alkyloxyalkyl; arylalkyl; Het-alkyl; mono- or dialkylaminoalkyl; Het; or aryl; or $R^4$ and $R^5$ together with the nitrogen atom to which they are attached form a radical selected from the group consisting of pyrrolidino, piperidino, piperazino, morpholino, 4-thiomorpholino, 2,3-dihydroisoindol-1-yl, thiazolidin-3-yl, 1,2,3,6-tetrahydropyridyl, 1,4-diazacycloheptyl, 1-aza-4-oxacycloheptyl, 1,2,3,4-tetrahydroisoquinolin-2-yl, 2H-pyrrolyl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, optionally substituted with one or more substituents, each substituent independently selected from alkyl, haloalkyl, halo, arylalkyl, hydroxy, alkyloxy, amino, mono- or dialkylamino, alkylthio, alkyloxyalkyl, alkylthioalkyl, aryl, pyridyl or pyrimidinyl;

$R^6$ is aryl or Het;

$R^7$ is hydrogen, halo, alkyl, aryl or Het;

$R^8$ is a straight or branched saturated hydrocarbon radical having from 1 to 6 carbon atoms;

R⁹ is hydrogen or alkyl; and

X is —CH₂— or —CO—;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with cyano, hydroxy, alkyloxy or oxo;

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, carboxyl, alkyloxycarbonyl, aminocarbonyl, morpholinyl or mono- or dialkylaminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, alkyl or alkyloxy;

halo is a substituent selected from fluoro, chloro, bromo or iodo; and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms.

2. A compound according to claim 1, characterized in that p is 0 or 1; R¹ is halo or alkyl; R² is alkyloxy or aryl; R³ is aryl, arylalkyl or Het-alkyl; q is 1; R⁴ and R⁵ each independently are alkyl or R⁴ and R⁵ together with the nitrogen atom to which they are attached form a 4-thiomorpholino, piperidino or piperazino radical substituted with alkyl or arylalkyl; R⁶ is aryl optionally substituted with a halo, or R⁶ is benzofuranyl; R⁷ is hydrogen; and R⁸ is a straight or branched saturated hydrocarbon radical having from 1 to 4 carbon atoms.

3. A compound according to claim 1, characterized in that p is 1; Z is a radical of formula (a); R¹ is bromo or methyl; R² is methyloxy or phenyl; R³ is phenyl optionally substituted with methyloxy, or benzyl; q is 1; R⁴ and R⁵ each are methyl, ethyl or isopropyl, or R⁴ and R⁵ together with the nitrogen atom to which they are attached form a 4-thiomorpholino radical, a piperidino radical substituted with methyl at the 4-position or a piperazino radical substituted with benzyl at the 4-position; R⁶ is phenyl or benzofuranyl; and R⁷ is hydrogen.

4. A compound according to claim 2, characterized in that p is 0 or 1; R¹ is bromo or methyl; R² is methyloxy or phenyl; R³ is phenyl, benzyl or quinoline-5-ylmethyl; q is 1; R⁴ and R⁵ each are methyl or R⁴ and R⁵ together with the nitrogen atom to which they are attached form a piperazino radical substituted with methyl at the 4-position; R⁶ is phenyl optionally substituted with a fluoro in the 2-position; R⁷ is hydrogen; and R⁸ is ethyl.

5. A compound selected from:
2-{benzyl-[(6-methyl-2-phenyl-quinolin-3-yl)-phenyl-methyl]-amino}-N-(4-methyl-piperazin-1-yl)-acetamide;
N-[(6-bromo-2-methoxy-quinolin-3-yl)-phenyl-methyl]-N',N'-dimethyl-N-phenyl-ethane-1,2-diamine;
N-benzyl-N-[(6-bromo-2-phenyl-quinolin-3-yl)-phenyl-methyl]-N',N'-dimethyl-ethane-1,2-diamine;
2-{benzyl-[(6-methyl-2-phenyl-quinolin-3-yl)-phenyl-methyl]-amino}-1-(4-methyl-piperazin-1-yl)-ethanone;
2-{[(6-bromo-2-methoxy-quinolin-3-yl)-phenyl-methyl]-quinolin-5-ylmethyl-amino}-1-(4-methyl-piperazin-1-yl)-ethanone;
2-{benzyl-[(6-bromo-2-methoxy-quinolin-3-yl)-phenyl-methyl]-amino}-1-(4-methyl-piperazin-1-yl)-ethanone;
N-benzyl-N-[(6-bromo-2-methoxy-quinolin-3-yl)-(2-fluoro-phenyl)-methyl]-N',N'-dimethyl-ethane-1,2-diamine;
{benzyl-[(6-bromo-2-methoxy-quinolin-3-yl)-phenyl-methyl]-amino}-acetic acid ethyl ester; and
2-{benzyl-[(6-methyl-2-phenyl-quinolin-3-yl)-phenyl-methyl]-amino}-1-piperidin-1-yl-ethanone;
a pharmaceutically acceptable acid or base addition salt thereof, a quaternary amine thereof, a stereochemically isomeric form thereof, a tautomeric form thereof, or a N-oxide form thereof.

6. A compound selected from:
2-{benzyl-[(6-methyl-2-phenyl-quinolin-3-yl)-phenyl-methyl]-amino}-1-(4-benzyl-piperazin-1-yl)-ethanone;
N-[(6-bromo-2-methoxy-quinolin-3-yl)-phenyl-methyl]-N-(2-methoxy-phenyl)-N',N'-dimethyl-ethane-1,2-diamine;
2-{benzyl-[(6-methyl-2-phenyl-quinolin-3-yl)-phenyl-methyl]-amino}-N,N-dimethyl-acetamide;
N-benzyl-N-[(6-bromo-2-phenyl-quinolin-3-yl)-phenyl-methyl]-N',N'-dimethyl-ethane-1,2-diamine;
2-{benzyl-[(6-methyl-2-phenyl-quinolin-3-yl)-phenyl-methyl]-amino}-1-(4-methyl-piperidin-1-yl)-ethanone;
2-{benzyl-[(6-methyl-2-phenyl-quinolin-3-yl)-phenyl-methyl]-amino}-N,N-diethyl-acetamide;
2-{benzyl-[(6-bromo-2-phenyl-quinolin-3-yl)-phenyl-methyl]-amino}-N,N-dimethyl-acetamide;
2-{[benzofuran-2-yl-(2-phenyl-quinolin-3-yl)-methyl]-benzyl-amino}-N-isopropyl-N-methyl-acetamide;
2-{benzyl-[(6-methyl-2-phenyl-quinolin-3-yl)-phenyl-methyl]-amino}-1-thiomorpholin-4-yl-ethanone; and
2-{benzyl-[(6-methyl-2-phenyl-quinolin-3-yl)-phenyl-methyl]-amino}-N-isopropyl-N-methyl-acetamide;
a pharmaceutically acceptable acid or base addition salt thereof, a quaternary amine thereof, a stereochemically isomeric form thereof, a tautomeric form thereof, or a N-oxide form thereof.

7. A composition comprising a pharmaceutically acceptable carrier and, as active ingredient, a therapeutically effective amount of a compound as defined in claim 1.

8. Method of treating a patient suffering from a bacterial disease, which comprises administering to the patient a therapeutically effective amount of a compound according to claim 1.

9. A composition comprising a pharmaceutically acceptable carrier and, as active ingredient, a therapeutically effective amount of a compound as defined in claim 5.

10. Method of treating a patient suffering from a bacterial disease, which comprises administering to the patient a therapeutically effective amount of a compound according to claim 5.

11. A composition comprising a pharmaceutically acceptable carrier and, as active ingredient, a therapeutically effective amount of a compound as defined in claim 6.

12. Method of treating a patient suffering from a bacterial disease, which comprises administering to the patient a therapeutically effective amount of a compound according to claim 6.

* * * * *